(12) United States Patent
Liang et al.

(10) Patent No.: US 8,202,866 B2
(45) Date of Patent: *Jun. 19, 2012

(54) ORTHO-AMINOANILIDES FOR THE TREATMENT OF CANCER

(75) Inventors: Chungen Liang, Shanghai (CN); Guozhi Tang, Shanghai (CN); Jason Christopher Wong, Shanghai (CN); Xihan Wu, Shanghai (CN)

(73) Assignee: Hoffmann-La Roche Inc., Nutley, NJ (US)

( * ) Notice: Subject to any disclaimer, the term of this patent is extended or adjusted under 35 U.S.C. 154(b) by 318 days.

This patent is subject to a terminal disclaimer.

(21) Appl. No.: 12/543,527

(22) Filed: Aug. 19, 2009

(65) Prior Publication Data

US 2010/0069328 A1  Mar. 18, 2010

(30) Foreign Application Priority Data

Sep. 17, 2008 (EP) .................................... 08164509

(51) Int. Cl.
*A61K 31/5375* (2006.01)
*C07D 265/30* (2006.01)

(52) U.S. Cl. ...................... 514/237.8; 544/106; 544/162; 546/184; 546/246; 548/566; 548/567; 514/231.2; 514/315; 514/428

(58) Field of Classification Search .................. 544/106, 544/162; 546/184, 246; 548/566, 567; 514/231.2, 514/237.8, 315, 428
See application file for complete search history.

(56) References Cited

U.S. PATENT DOCUMENTS 7,795,315 B2 *  9/2010  Chen et al. .................... 514/616

FOREIGN PATENT DOCUMENTS

| DE | 2062265 | 5/1972 |
|---|---|---|
| WO | WO 2007/087130 | 8/2007 |
| WO | WO 2007/100657 | 9/2007 |
| WO | 2009/095324 | 8/2009 |

OTHER PUBLICATIONS

Koyama et al., Blood, vol. 96, pp. 1490-1495 (2000).
Martin, et al., Ongogene, vol. 26, pp. 5450-5467 (2007).
Matsuoka et al., Biochemical Pharmacology vol. 74, pp. 465-476 (2007).
Abstract corresponding to Document B3 (DE2062265), 1972.

* cited by examiner

*Primary Examiner* — Golam M M Shameem
(74) *Attorney, Agent, or Firm* — George W. Johnston; Patricia S. Rocha-Tramaloni

(57) ABSTRACT

The present invention is directed to a compound of formula I, (I)

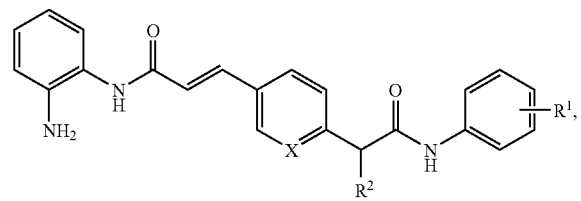

and processes for the manufacture of said compounds as well as medicaments containing said compound. The compounds according to this invention show anti-proliferative and differentiation-inducing activity and are thus useful for the treatment of diseases such as cancer in humans or animals.

6 Claims, No Drawings

ORTHO-AMINOANILIDES FOR THE TREATMENT OF CANCER

PRIORITY TO RELATED APPLICATION(S)

This application claims the benefit of European Patent Application No. 08164509.5, filed Sep. 17, 2008, which is hereby incorporated by reference in its entirety.

FIELD OF THE INVENTION

The invention relates to novel antitumor agents and pharmaceutically acceptable salts thereof, and processes for the manufacture of these novel compounds and medicaments containing them. The compounds of the invention have antiproliferative and differentiation-inducing activity, which results in inhibition of tumor cell proliferation, induction of apoptosis and inhibition of invasion. The invention concerns thus also the use of such compounds for the treatment of diseases such as cancer and for the manufacture of corresponding medicaments.

The compounds according to this invention are inhibitors of histone deacetylase (HDAC) and therefore show antiproliferative and differentiation-inducing activity, which results in inhibition of tumor cell proliferation, induction of apoptosis and inhibition of invasion.

BACKGROUND OF THE INVENTION

Transcriptional regulation is a major event in cell differentiation, proliferation, and apoptosis. Transcriptional activation of a set of genes determines cell destination and for this reason transcription is tightly regulated by a variety of factors. One of its regulatory mechanisms involved in the process is an alteration in the tertiary structure of DNA, which affects transcription by modulating the accessibility of transcription factors to their target DNA segments. Nucleosomal integrity is regulated by the acetylation status of the core histones. In a hypoacetylated state, nucleosomes are tightly compacted and thus are nonpermissive for transcription. On the other hand, nucleosomes are relaxed by acetylation of the core histones, with the result being permissiveness to transcription. The acetylation status of the histones is governed by the balance of the activities of histone acetyl transferase (HAT) and histone deacetylase (HDAC). Recently, HDAC inhibitors have been found to arrest growth and induce apoptosis in several types of cancer cells, including colon cancer cells, T-cell lymphoma cells, and erythroleukemic cells. Given that apoptosis is a crucial factor for cancer progression, HDAC inhibitors are promising reagents for cancer therapy as effective inducers of apoptosis (Koyama, Y., et al., Blood 96 (2000) 1490-1495).

Histone deacetylases (HDACs) are the key enzymatic components of multiprotein complexes responsible for deacetylation of lysine residues in histone and nonhistone protein substrates. HDACs can be subdivided into three major classes according to their sequence homology to the yeast HDACs, Rpd3, Hda1, and Sir2. The class I HDACs (HDACs 1, 2, 3, and 8), homologous to Rpd3, localize primarily in the nucleus and appear to be expressed in most tissues. The class II HDACs (HDACs 4, 5, 6, 7, 9, 10), homologous to Hda1, are able to shuttle between the nucleus and the cytoplasm depending on a variety of regulatory signals and cellular state, and have tissue-specific expression patterns. These HDACs can be further subdivided into class IIa (HDACs 4, 5, 7, 9), and class IIb (HDACs 6, 10). The class III HDACs, homologous to Sir2, are $NAD^+$-dependent deacetylases that are mechanistically distinct from the class I and II HDACs and are not inhibited by classical HDAC inhibitors such as trichostatin A, trapoxin B, or SNDX-275. The HDACs can thus be divided into three classes on the basis of sequence similarity, cellular localization tendencies, tissue expression patterns, and enzymatic mechanism.

The class I HDACs in particular have been closely associated with antiproliferative effects against tumor cells. For example, pharmacological inhibition of HDACs 1-3 leads to induction of the cyclin-dependent kinase inhibitor p21 and concomitant cell cycle arrest. The class IIa HDACs are known to associate with the HDAC3/SMRT/N-CoR complex and MEF2 and as such have important roles in regulating muscle cell gene expression (reviewed in *Oncogene* 2007, 26, 5450-5467) and the immune response (*Biochemical Pharmacology* 2007, 74, 465-476). Due to their specific antiproliferative function, selective inhibition of the class I HDACs may be desirable to achieve antitumor efficacy with lower toxicity.

The compounds of the present invention show enhanced potency toward class I HDACs and enhanced antiproliferative efficacy versus cancer cells as compared to SNDX-275, a structurally-related HDAC inhibitor in clinical trials. Class I HDAC inhibitory potency is evaluated by a reporter gene assay that evaluates HDAC subtype activity in the context of relevant multiprotein complexes present in the cell that are typically absent in enzyme activity assays. Thus, the compounds of the present invention possess in-cell inhibitory potency toward class I HDACs that correlates to their improved anticancer efficacy in comparison to SNDX-275.

WO 2007/100657 describes related but structurally different o-phenylendiamine derivatives as cell differentiation inducers. The same type of compounds is also the subject of WO2007/087130. The compounds described in these applications are exclusively o-phenylene derivatives monoacylated with derivatives of benzoic acid. However there remains a need for new compounds with improved therapeutic properties, such as enhanced activity, decreased toxicity, better solubility and/or improved pharmacokinetic profile, to name only a few.

Monoacylated o-phenylendiamines are known in the art as precursors for the preparation of the corresponding benzimidazoles, such preparation methods are e.g. described in DE-A 2 062 265; FR 2 167 954; Rastogi, R., and Sharma, S., Indian J. Chem., Sect. B, 21B (5) (1982) 485-487; Moll, R., et al., Z. Chem. 17 (1977) 133-134; and Hassan, H., et al., Indian J. Chem. 39B (2000) 764-768.

It has been found that the compounds of the present invention are HDAC inhibitors which have anti-proliferative and differentiation-inducing activity, which results in inhibition of tumor cell proliferation, induction of apoptosis and inhibition of invasion. These compounds are therefore useful for the treatment of diseases such as cancer in humans or animals.

SUMMARY OF THE INVENTION

The present invention is directed to the compounds of formula I, (I)

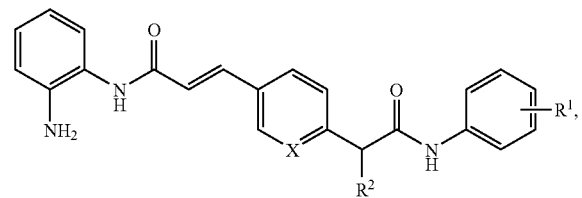

wherein
R¹ is selected from the group consisting of:
  hydrogen;
  halogen;
  lower alkyl, unsubstituted or once or several times substituted by halogen;
  cycloalkyl;
  cyano;
  lower alkoxy;
R² is —(CH₂)ₙ—R³ or —NR⁴R⁵;
R³ is a 3 to 10-membered heterocyclyl ring, unsubstituted or once or several times substituted by halogen, lower alkyl, hydroxy, —C(O)-lower alkyl, =O, or NR⁴R⁵;
R⁴ is hydrogen or lower alkyl;
R⁵ is hydrogen or lower alkyl;
n is 0, 1, 2, or 3; and
X is C or N.

The present invention is also directed to pharmaceutically active salts, racemic mixtures, enantiomers, optical isomers and tautomeric forms of the above compound.

The present invention also encompasses pharmaceutically acceptable salts and prodrugs of the compounds of formula (I) as well as the use of these compounds to produce medicaments.

The present invention also relates to a pharmaceutical composition comprising a compound according to formula I or a pharmaceutically-active salt, racemic mixture, enantiomer, optical isomer, or tautomeric form thereof.

The compounds according to this invention are inhibitors of histone deacetylase (HDAC) and therefore show antiproliferative and differentiation-inducing activity, which results in inhibition of tumor cell proliferation, induction of apoptosis and inhibition of invasion.

DETAILED DESCRIPTION OF THE INVENTION

The term "lower alkyl" as used herein denotes a saturated, linear- or branched chain alkyl group containing 1 to 8, preferably 1 to 6, more preferably 1 to 4 carbon-atoms, for example methyl, ethyl, propyl, isopropyl, 1-butyl, 2-butyl, tert-butyl and the like. Preferred "C₁-C₈-alkyl" groups have 1, 2 or 3 carbon-atoms.

The term "lower alkoxy" as used herein denotes a group —O-alkyl, wherein the alkyl is a "lower alkyl" group as defined above; for example, methoxy, ethoxy, propoxy, isopropoxy, n-butoxy, i-butoxy, 2-butoxy, t-butoxy and the like. Preferred alkoxy groups are groups with 1-4 carbon atoms.

The term "cycloalkyl" as used herein means a saturated, cyclic hydrocarbon consisting of one or two rings, which may be fused or attached via a single bond, and containing from 3 to 8, preferably from 3 to 6 carbon atoms. Examples of such 3 to 8 membered cycloalkyl rings are cyclopropyl, cyclobutyl, cyclopentyl, cyclohexyl, cyclooctyl, octahydro-indene, bicyclo[2.2.1]heptane, bicyclohexyl and the like.

The term "heterocyclyl" as used herein means a 3 to 8 membered mono- or bicyclic cycloalkyl as defined above, wherein up to four carbon atoms, preferably one, two or three carbon atoms are replaced by oxygen, nitrogen or sulphur. Examples include but are not limited to morpholinyl, thiomorpholinyl, piperidinyl, piperazinyl, tetrahydro-pyranyl, 2-Oxa-5-aza-bicyclo[2.2.1]heptanyl, [1,4]oxathianyl, azepanyl, [1,4]diazepanyl, pyrrolidinyl, pyrazolidinyl, [1,2,3]triazolidinyl, imidazolidinyl, thiazolidinyl, azetidinyl.

The term "halogen" means fluorine, chlorine, bromine or iodine.

The term "several times substituted" as used herein means up to 5 times substituted, preferably up to 4 times, most preferably 2 or 3 times substituted.

The present invention is directed to the compounds of formula I,

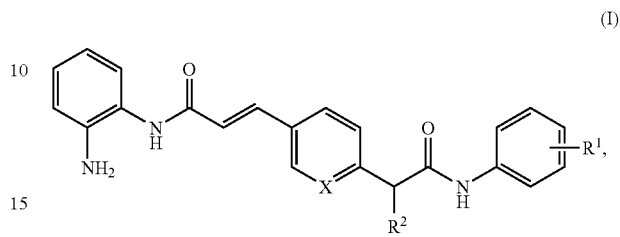

wherein
R¹ is selected from the group consisting of:
  hydrogen;
  halogen;
  lower alkyl, unsubstituted or once or several times substituted by halogen;
  cycloalkyl;
  cyano;
  lower alkoxy;
R² is —(CH₂)ₙ—R³ or —NR⁴R⁵;
R³ is a 3 to 10-membered heterocyclyl ring, unsubstituted or once or several times substituted by halogen, lower alkyl, hydroxy, —C(O)-lower alkyl, =O, or NR⁴R⁵;
R⁴ is hydrogen or lower alkyl;
R⁵ is hydrogen or lower alkyl;
n is 0, 1, 2, or 3; and
X is C or N.

Compounds of the general formula I which contain one or several chiral centers can either be present as racemates, diastereomeric mixtures, or optically active single isomers. The racemates can be separated according to known methods into the enantiomers. Preferably, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et. al., Organic Process Research & Development 2000, 4, 427-435; or in Ansel, H., et. al., In: Pharmaceutical Dosage Forms and Drug Delivery Systems, 6th ed. (1995), pp. 196 and 1456-1457.

In one preferred embodiment according to the present invention, the compound is a compound of formula (I) as defined above, wherein $R^1$ is selected from the group consisting of:
  halogen;
  lower alkyl, unsubstituted or once or several times substituted by halogen; and
  cycloalkyl.

In another preferred embodiment according to the present invention, the compound is a compound of formula (I) as defined herein before, wherein X is C.

In still another preferred embodiment according to the present invention, the compound is a compound of formula (I) as defined above, wherein $R^3$ is selected from the group consisting of: pyrrolidinyl, morpholinyl, piperidinyl, thiomorpholinyl, and 2-oxa-5-aza-bicyclo[2.2.1]heptanyl, wherein all the aforementioned rings may be unsubstituted or once or several times substituted by halogen, lower alkyl, hydroxy, —C(O)-lower alkyl, =O, or $NR^4R^5$; or $NR^4R^5$.

The following specific compounds are especially preferred according to the present invention:
2-{4-[(E)-2-(2-Amino-phenylcarbamoyl)-vinyl]-phenyl}-5-morpholin-4-yl-pentanoic acid (4-bromo-phenyl)-amide;
2-{4-[(E)-2-(2-Amino-phenylcarbamoyl)-vinyl]-phenyl}-5-(1S,4S)-2-oxa-5-aza-bicyclo[2.2.1]hept-5-yl-pentanoic acid (4-trifluoromethyl-phenyl)-amide;
2-{4-[(E)-2-(2-Amino-phenylcarbamoyl)-vinyl]-phenyl}-5-(1S,4S)-2-oxa-5-aza-bicyclo[2.2.1]hept-5-yl-pentanoic acid (4-bromo-phenyl)-amide;
2-{4-[(E)-2-(2-Amino-phenylcarbamoyl)-vinyl]-phenyl}-5-morpholin-4-yl-pentanoic acid (4-isopropyl-phenyl)-amide;
2-{4-[(E)-2-(2-Amino-phenylcarbamoyl)-vinyl]-phenyl}-5-(1S,4S)-2-oxa-5-aza-bicyclo[2.2.1]hept-5-yl-pentanoic acid (4-isopropyl-phenyl)-amide;
2-{4-[(E)-2-(2-Amino-phenylcarbamoyl)-vinyl]-phenyl}-5-(3-hydroxy-piperidin-1-yl)-pentanoic acid (4-isopropyl-phenyl)-amide;
2-{4-[(E)-2-(2-Amino-phenylcarbamoyl)-vinyl]-phenyl}-5-(3-hydroxy-piperidin-1-yl)-pentanoic acid (4-bromo-phenyl)-amide;
2-{4-[(E)-2-(2-Amino-phenylcarbamoyl)-vinyl]-phenyl}-N-(4-bromo-phenyl)-4-morpholin-4-yl-butyramide;
2-{4-[(E)-2-(2-Amino-phenylcarbamoyl)-vinyl]-phenyl}-5-pyrrolidin-1-yl-pentanoic acid (4-trifluoromethyl-phenyl)-amide;
2-{4-[(E)-2-(2-Amino-phenylcarbamoyl)-vinyl]-phenyl}-5-piperidin-1-yl-pentanoic acid (4-bromo-phenyl)-amide;
2-{4-[(E)-2-(2-Amino-phenylcarbamoyl)-vinyl]-phenyl}-5-pyrrolidin-1-yl-pentanoic acid (4-bromo-phenyl)-amide;
2-{4-[(E)-2-(2-Amino-phenylcarbamoyl)-vinyl]-phenyl}-5-(2-oxa-5-aza-bicyclo[2.2.1]hept-5-yl)-pentanoic acid (4-chloro-phenyl)-amide;
(E)-N-(2-Amino-phenyl)-3-{4-[1-(4-chloro-phenylcarbamoyl)-2-(3-diethylamino-pyrrolidin-1-yl)-ethyl]-phenyl}-acrylamide;
2-{4-[(E)-2-(2-Amino-phenylcarbamoyl)-vinyl]-phenyl}-N-(4-bromo-phenyl)-4-(3-hydroxy-piperidin-1-yl)-butyramide;
2-{4-[(E)-2-(2-Amino-phenylcarbamoyl)-vinyl]-phenyl}-N-(4-bromo-phenyl)-4-(1S,4S)-2-oxa-5-aza-bicyclo[2.2.1]hept-5-yl-butyramide;
2-{4-[(E)-2-(2-Amino-phenylcarbamoyl)-vinyl]-phenyl}-N-(4-bromo-phenyl)-4-(1-methyl-pyrrolidin-2-yl)-butyramide; and
(E)-N-(2-Amino-phenyl)-3-{4-[1-(4-bromo-phenylcarbamoyl)-2-(1-methyl-piperidin-4-yl)-ethyl]-phenyl}-acrylamide.

The compounds according to the present invention show valuable pharmaceutical properties, in particular as anti-proliferative or anti-cancer agents, more specifically as agents for the treatment of solid tumors and hematological tumors.

Therefore, in another embodiment according to the present invention, there is provided a pharmaceutical composition comprising at least one compound as defined herein before together with pharmaceutically acceptable adjuvants.

In another embodiment according to the present invention, there is provided a compound as defined above for use as a medicament.

In still another embodiment according to the present invention, there is provided a compound as defined above for use in the treatment of cancer, in particular solid tumors and hematological tumors, more particularly leukemia, lymphoma, colon, liver, or gastric cancer.

In yet another embodiment according to the present invention, there is provided the use of at least one compound as defined above for the manufacture of medicaments for the treatment of cancer, in particular solid tumors and hematological tumors. Said medicaments, e.g. in the form of pharmaceutical preparations, can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The above-mentioned pharmaceutical preparations can be obtained by processing the compounds according to this invention with pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage depends on various factors such as manner of administration, species, age and/or individual state of health. The doses to be administered daily are about 5-400 mg/kg, preferably about 10-100 mg/kg, and can be taken singly or distributed over several administrations.

In another preferred embodiment according to the present invention, there is provided a method of treating cancer in a patient comprising administering to said patient at least one compound according to the present invention.

The compounds of the present invention as well as their starting materials can be synthesized according to the following general reaction schemes 1 to 8, respectively. In said reaction schemes 1 to 8, all substituents, in particular $R^1$ to $R^5$, have the meanings given herein before unless explicitly otherwise stated. Furthermore, and unless explicitly otherwise stated, all reactions, reaction conditions, abbreviations and symbols have the meanings well known to a person of ordinary skill in organic chemistry.

Abbreviations
bp: boiling point
dba: dibenzylidene acetone
DIPEA: diisopropylethylamine
DMEM: Dulbecco's Modified Eagle Medium
DMF: dimethylformamide
DMSO: dimethylsulfoxide
DNA: deoxyribonucleic acid
EDCI: 1-ethyl-3-(3-dimethylaminopropyl)carbodiimide
ELISA: enzyme-linked immunosorbent assay
EtOAc: ethyl acetate
FBS: fetal bovine serum
g: gram
GFP: green fluorescent protein
$GI_{50}$: concentration required for 50% growth inhibition
$GI_{90}$: concentration required for 90% growth inhibition
h: hour
HATU: O-(7-azabenzotriazol-1-yl)-N,N,N',N'-tetramethyluronium hexafluorophosphate
HDAC: histone deacetylase
HOAc: acetic acid
HOBt: 1-hydroxybenzotriazole
HPLC: high performance liquid chromatography
Hz: Hertz
MeOD: deuterated methanol
MeOH: methanol
mg: milligram
MHz: megahertz
mL: milliliter
mmol: millimole
MsCl: methanesulfonyl chloride
MTS: 3-(4,5-dimethylthiazol-2-yl)-5-(3-carboxymethoxyphenyl)-2-(4-sulfophenyl)-2H-tetrazolium)
MW: molecular weight
nL: nanoliter
NMR: nuclear magnetic resonance
O/N: overnight
PET: petroleum ether
Pybrop: bromo-tris-pyrrolidino-phosphoniumhexafluorophosphate
rt: room temperature
TBS: tert-butyldimethylsilyl
t-BuOK: potassium tert-butoxide
THF: tetrahydrofuran
TLC: thin layer chromatography
uL: microliter
WST: 4-[3-(4-iodophenyl)-2-(4-nitrophenyl)-2H-5-tetrazolio]-1,3-benzene disulfonate A. General Synthetic Route for Synthesis of Two-Carbon Link-Cinnamides (Scheme 1)

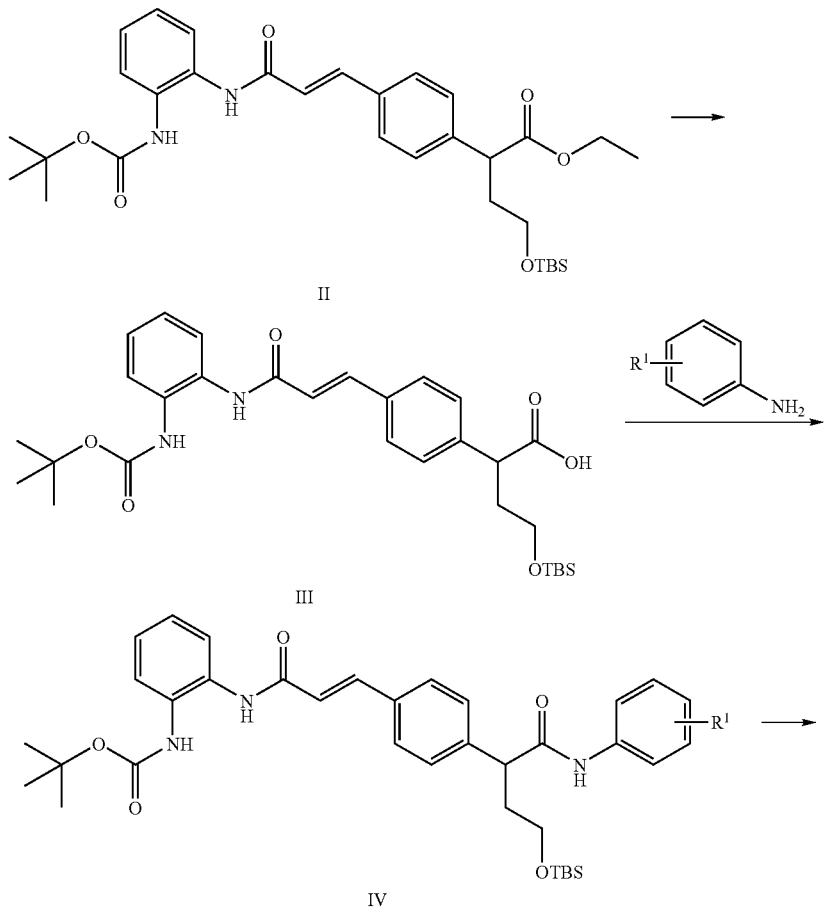

Scheme 1

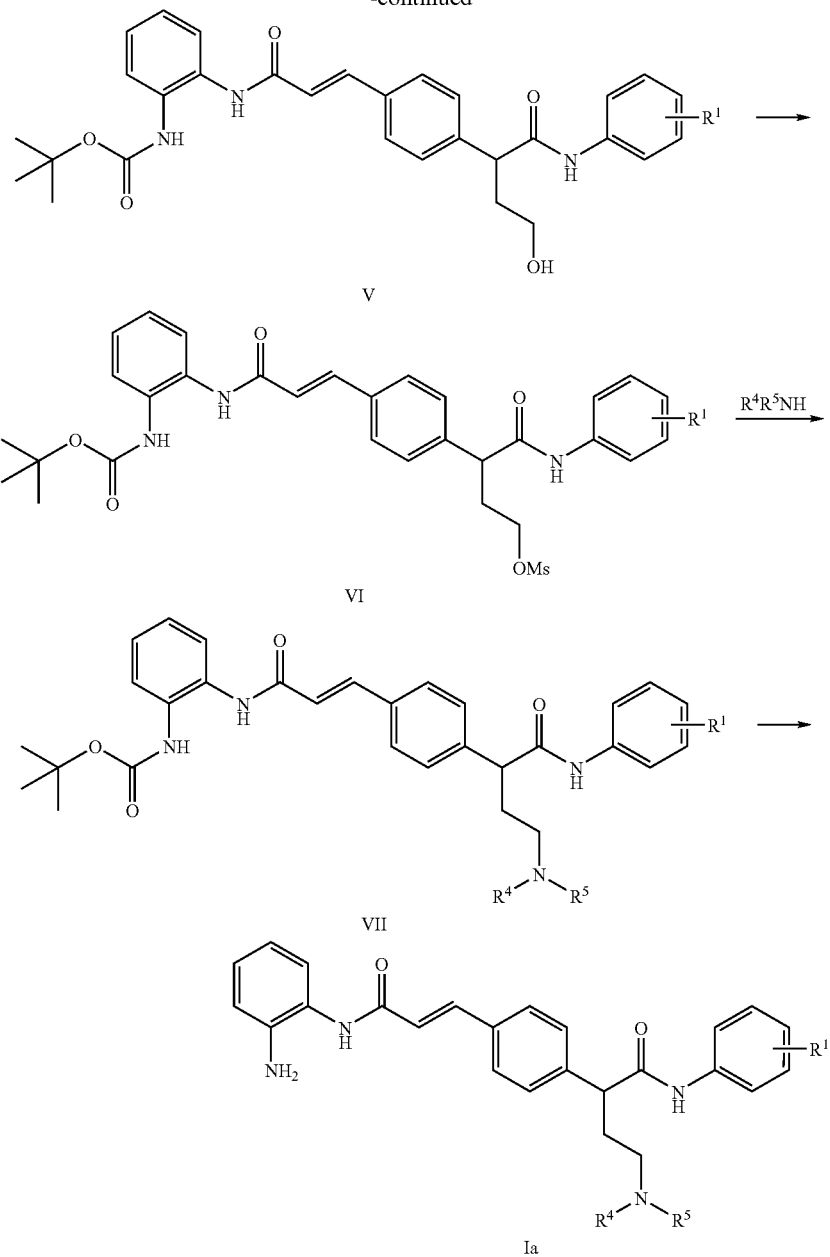

Compounds of interest Ia can be prepared according to Scheme 1. Starting with ester II (see Scheme 6 for preparation of II), hydrolysis with lithium hydroxide gives acid III. Coupling of various anilines to III provides anilides IV, which are deprotected by fluoride anion to provide alcohols V. Sulfonylation of alcohols V with methanesulfonyl chloride furnishes mesylates VI, which can then undergo nucleophilic substitution with various amines to give compounds VII. Compounds VII can be deprotected under acidic conditions to obtain compounds of interest Ia.

2-{4-[2-(2-tert-Butoxycarbonylamino-phenylcarbamoyl)-vinyl]-phenyl}-4-hydroxy-butyric acid ethyl ester (II) can be prepared according to the synthetic route outlined in Scheme 6.

2-{4-[2-(2-tert-Butoxycarbonylamino-phenylcarbamoyl)-vinyl]-phenyl}-4-hydroxy-butyric acid (III) can be prepared from hydrolysis of II. The reaction can be carried out with aqueous lithium hydroxide mixed with a suitable organic solvent such as methanol or tetrahydrofuran, typically at room temperature over several hours.

Anilide compounds IV can be prepared from coupling various amines with 2-{4-[2-(2-tert-butoxycarbonylamino-phenylcarbamoyl)-vinyl]-phenyl}-4-hydroxy-butyric acid (III). The reaction is typically performed with standard peptide coupling reagents such as EDCI and HOBt, Pybrop and diisopropylethylamine, or HATU and triethylamine in a suitable inert solvent such as dichloromethane or dimethylformamide or mixtures thereof at room temperature for several hours.

Alcohol compounds V can be prepared from fluoride-mediated deprotection of anilide compounds IV. The reaction is typically carried out with fluoride anion sources such as tetrabutylammonium fluoride or tetrabutylammonium dihydrogen trifluoride in tetrahydrofuran at room temperature for eight to twelve hours.

Mesylate compounds VI can be prepared by reacting alcohol compounds V with methanesulfonyl chloride. The reaction is typically performed at zero degrees Celsius for 30 minutes to a couple of hours in dichloromethane with a suitable amine base such as diisopropylethylamine or triethylamine.

Compounds VII can be prepared by nucleophilic substitution of mesylate compounds VI with various amines. The reaction is typically carried out in a suitable inert solvent such as dichloromethane or acetonitrile with an amine base such as diisopropylethylamine or triethylamine at temperatures ranging from room temperature to reflux over several hours.

Compounds of interest Ia are obtained by deprotection of compounds VII. The reaction is typically performed in methanolic hydrogen chloride at room temperature over several hours.

B. General Synthetic Route for Synthesis of Three-Carbon Link-Cinnamides (Scheme 2, 3)

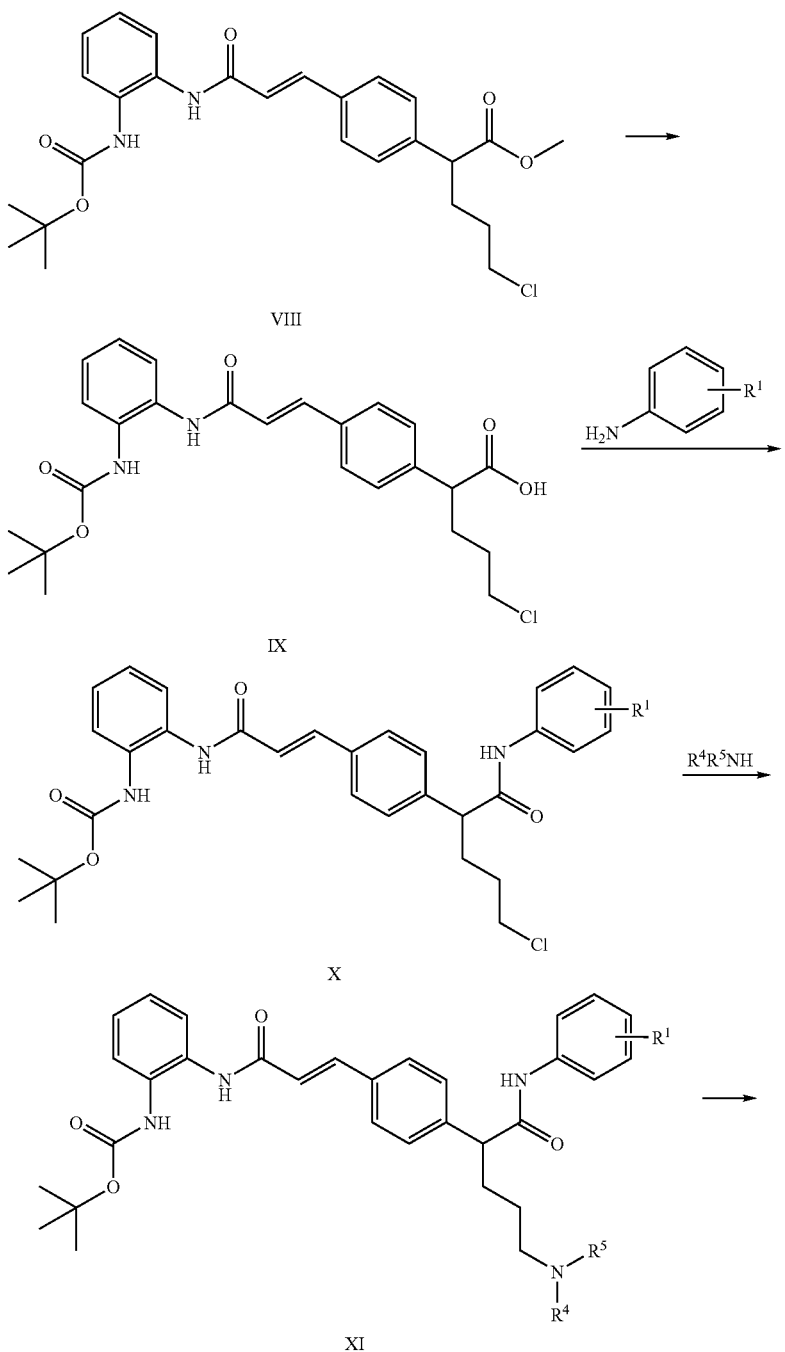

Scheme 2

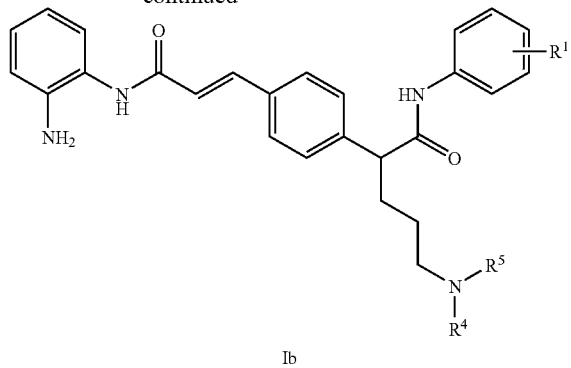

Ib

Compounds of interest Ib can be prepared according to Scheme 2. Starting with ester VIII (see Scheme 7 for preparation of VIII), hydrolysis with lithium hydroxide gives acid IX. Coupling of various anilines to IX provides anilides X, which can then undergo nucleophilic substitution with various amines to give compounds XI. Compounds XI can be deprotected under acidic conditions to obtain compounds of interest Ibo.

2-{4-[2-(2-tert-Butoxycarbonylamino-phenylcarbamoyl)-vinyl]-phenyl}-5-chloro-pentanoic acid methyl ester (VIII) can be prepared according to the synthetic route outlined in Scheme 7.

2-{4-[2-(2-tert-Butoxycarbonylamino-phenylcarbamoyl)-vinyl]-phenyl}-5-chloro-pentanoic acid (IX) can be prepared from hydrolysis of VIII. The reaction can be carried out with aqueous lithium hydroxide mixed with a suitable organic solvent such as methanol or tetrahydrofuran, typically at room temperature over several hours.

Anilide compounds X can be prepared from coupling various anilines with 2-{4-[2-(2-tert-Butoxycarbonylamino-phenylcarbamoyl)-vinyl]-phenyl}-5-chloro-pentanoic acid (IX). The reaction is typically performed with standard peptide coupling reagents such as EDCI and HOBt, Pybrop and diisopropylethylamine, or HATU and triethylamine in a suitable inert solvent such as dichloromethane or dimethylformamide or mixtures thereof at room temperature for several hours.

Compounds XI can be prepared from nucleophilic substitution of anilide compounds X with various amines. The reaction is typically carried out in a suitable inert solvent such as dimethylformamide with excess amine at 70 to 80 degrees Celsius for eight to sixteen hours.

Compounds of interest Ib are obtained by deprotection of compounds XI. The reaction is typically performed in methanolic hydrogen chloride at room temperature over several hours.

Scheme 3

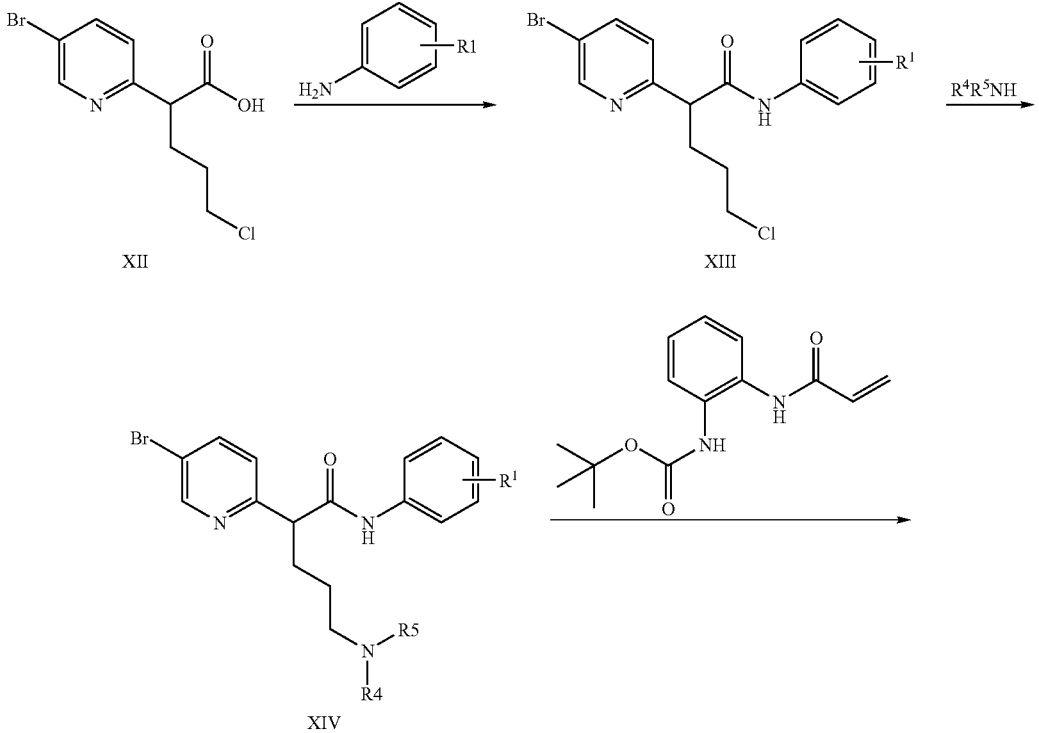

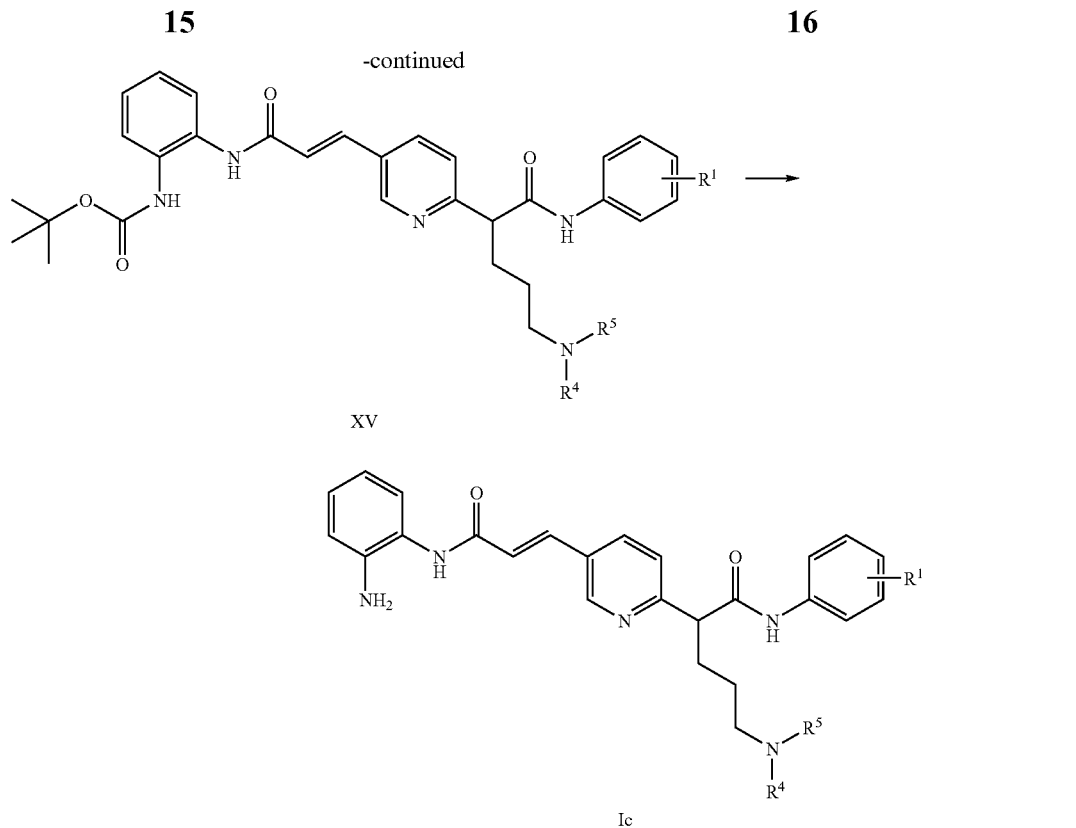

XV

Ic

Compounds of interest Ic can be prepared according to Scheme 3. Starting with acid XII (see Scheme 8 for preparation of XII), coupling of various anilines to XII provides anilides XIII, which can then undergo nucleophilic substitution with various amines to give compounds XIV. Subsequent Heck reaction of compounds XIV with (2-acryloylaminophenyl)-carbamic acid tert-butyl ester furnishes compounds XV, which can be deprotected under acidic conditions to obtain compounds of interest Ic.

2-(5-Bromo-pyridin-2-yl)-5-chloro-pentanoic acid (XII) can be prepared according to the synthetic route outlined in Scheme 8.

Anilide compounds XIII can be prepared from coupling various anilines with 2-(5-bromo-pyridin-2-yl)-5-chloro-pentanoic acid (XII). The reaction is typically performed with standard peptide coupling reagents such as EDCI and HOBt, Pybrop and diisopropylethylamine, or HATU and triethylamine in a suitable inert solvent such as dichloromethane or dimethylformamide or mixtures thereof at room temperature for several hours.

Compounds XIV can be prepared from nucleophilic substitution of anilide compounds XIII with various amines. The reaction is typically carried out in a suitable inert solvent such as dimethylformamide with excess amine at 70 to 80 degrees Celsius for eight to sixteen hours.

Compounds XV can be prepared by Heck reaction of compounds XIV and (2-acryloylamino-phenyl)-carbamic acid tert-butyl ester. The reaction is typically performed in deoxygenated dimethylformamide with triethylamine, tri-ortho-tolyl-phosphine, $Pd_2(dba)_3$, at 80-100 degrees Celsius for about ten to fifteen hours under inert atmosphere.

Compounds of interest Ic are obtained by deprotection of compounds XV. The reaction is typically performed in methanolic hydrogen chloride at room temperature over several hours.

C. Synthesis of One or Two-Carbon Link-Cinnamides (Scheme 4 and 5)

Scheme 4

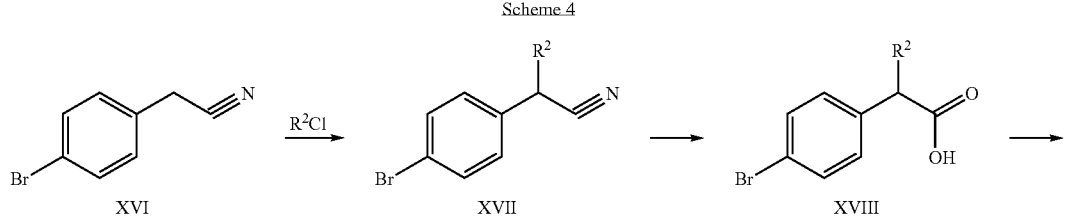

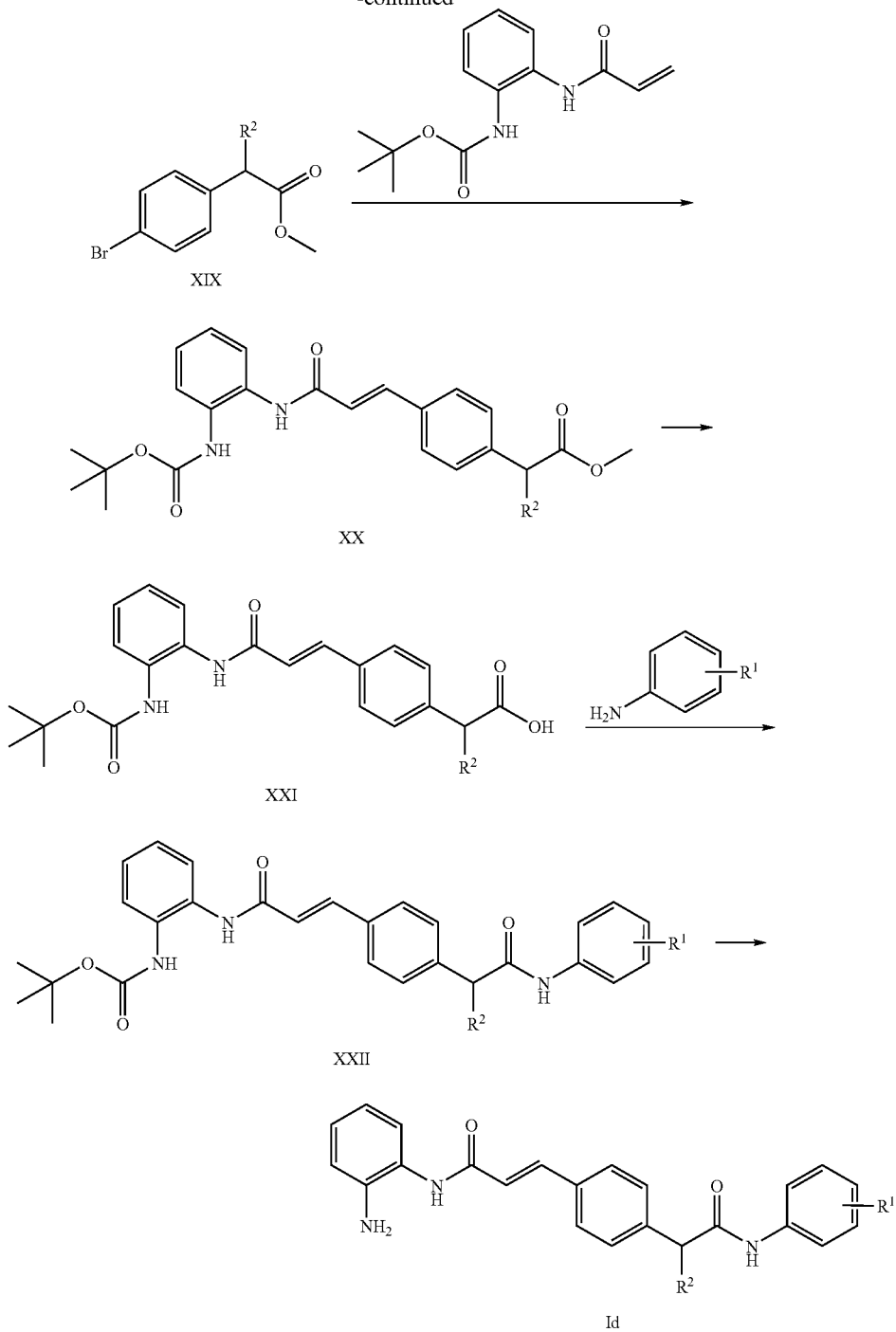

Compounds of interest Id can be prepared according to Scheme 4. Starting with commercially available nitrile XVI, deprotonation with base followed by alkylation with various alkyl chlorides gives compounds XVII. Acidic hydrolysis of compounds XVII gives acids XVIII, which can be subsequently converted to methyl esters XIX by nucleophilic acyl substitution. Heck reaction of compounds XIX with (2-acryloylamino-phenyl)-carbamic acid tert-butyl ester furnishes methyl ester compounds XX, which can be hydrolyzed under basic conditions to the corresponding acids XXI. Coupling of various anilines to acids XXI provides anilides XXII, which can be subsequently deprotected under acidic conditions to obtain compounds of interest Id.

(4-Bromo-phenyl)-acetonitrile (XVI) is commercially available.

Compounds XVII can be prepared from alkylation of deprotonated XVI with various alkyl chlorides. The reaction is typically performed by deprotonating XVI with a strong base such as sodium hydride in a mixture of inert solvents such as dimethylformamide and toluene at zero degrees Celsius for approximately one hour, followed by adding an alkyl chloride and heating to around 70-80 degrees Celsius for two hours.

Compounds XVIII can be prepared from acidic hydrolysis of the nitrile functional group in compounds XVII. The reaction is typically carried out in a mixture of concentrated sulfuric acid and water at reflux temperature for several hours.

Compounds XIX can be prepared by nucleophilic acyl substitution of compounds XVIII. The reaction is typically performed by reacting compounds XVIII with thionyl chloride in methanol at zero degrees Celsius followed by heating to reflux for several hours.

Compounds XX can be prepared by Heck reaction of compounds XIX and (2-acryloylamino-phenyl)-carbamic acid tert-butyl ester. The reaction is typically performed in deoxygenated dimethylformamide with triethylamine, tri-ortho-tolyl-phosphine, $Pd_2(dba)_3$, at 80-100 degrees Celsius for about four to ten hours under inert atmosphere.

Compounds XXI can be prepared from basic hydrolysis of compounds XX. The reaction can be carried out with aqueous lithium hydroxide mixed with a suitable organic solvent such as methanol or tetrahydrofuran, typically at room temperature over several hours.

Anilide compounds XXII can be prepared from coupling various anilines with compounds XXI. The reaction is typically performed with standard peptide coupling reagents such as EDCI and HOBt, Pybrop and diisopropylethylamine, or HATU and triethylamine in a suitable inert solvent such as dichloromethane or dimethylformamide or mixtures thereof at room temperature for several hours.

Compounds of interest Id are obtained by acidic deprotection of compounds XXII. The reaction is typically performed in methanolic hydrogen chloride at room temperature over several hours.

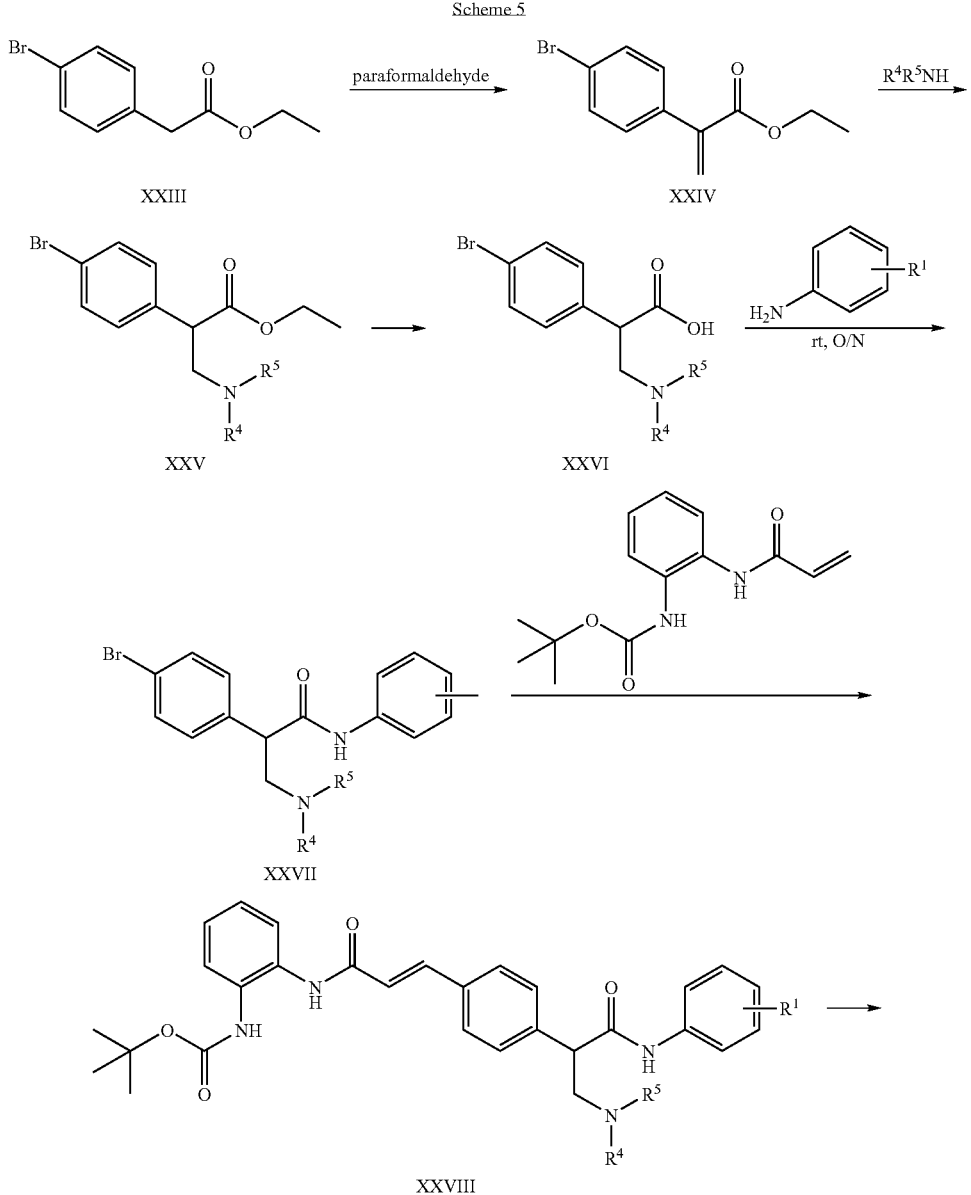

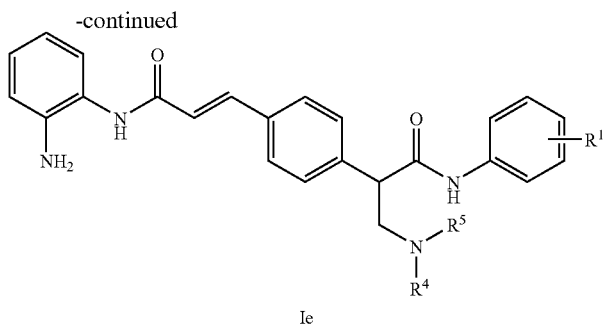

Ie

Compounds of interest Ie can be prepared according to Scheme 5. Starting with commercially available (4-bromophenyl)-acetic acid ethyl ester (XXIII), aldol condensation with paraformaldehyde furnishes 2-(4-bromo-phenyl)-acrylic acid ethyl ester (XXIV). Michael addition of various amines with XXIV provides compounds XXV, which are subsequently hydrolyzed under basic conditions to acids XXVI. Coupling of various anilines to compounds XXVI provides anilides XXVII. Heck reaction of compounds XXVII with (2-acryloylamino-phenyl)-carbamic acid tert-butyl ester gives compounds XXVIII, which are then deprotected under acidic conditions to furnish the compounds of interest, Ie.

(4-Bromo-phenyl)-acetic acid ethyl ester (XXIII) is commercially available.

2-(4-Bromo-phenyl)-acrylic acid ethyl ester (XXIV) can be prepared from aldol condensation of XXIII with paraformaldehyde. The reaction is typically performed by mixing XXIV with paraformaldehyde in dimethylformamide and a phase transfer catalyst such as tetrabutylammonium chloride with a suitable base such as potassium carbonate. The reaction is then heated to 60-70 degrees Celsius for several hours.

Compounds XXV can be prepared from Michael addition of various amines to XXIV. The reaction is typically carried out by adding an amine to XXV in tetrahydrofuran at zero degrees Celsius and then warming to room temperature over one to two hours.

Compounds XXVI can be prepared by basic hydrolysis of compounds XXV. The reaction is typically performed by heating compounds XXV with a suitable base such as aqueous lithium hydroxide or sodium hydroxide in methanol at forty degrees Celsius for several hours.

Anilide compounds XXVII can be prepared from coupling various anilines with compounds XXVI. The reaction is typically performed with standard peptide coupling reagents such as EDCI and HOBt, Pybrop and diisopropylethylamine, or HATU and triethylamine in a suitable inert solvent such as dichloromethane or dimethylformamide or mixtures thereof at room temperature for several hours.

Compounds XXVIII can be prepared by Heck reaction of compounds XXVI and (2-acryloylamino-phenyl)-carbamic acid tert-butyl ester. The reaction is typically performed in deoxygenated dimethylformamide with triethylamine, tri-ortho-tolyl-phosphine, $Pd_2(dba)_3$, at 80-100 degrees Celsius for about four to ten hours under inert atmosphere.

Compounds of interest Ie are obtained by acidic deprotection of compounds XXVIII. The reaction is typically performed in methanolic hydrogen chloride at room temperature over several hours.

Each method according to any of schemes 1 to 5 as disclosed herein before forms a particularly preferred embodiment according to the present invention.

D. Synthetic Routes for Key Building Blocks

Synthesis of (E)-2-{4-[2-(2-tert-Butoxycarbonylamino-phenylcarbamoyl)-vinyl]-phenyl}-4-(tert-butyl-dimethyl-silanyloxy)-butyric acid ethyl ester (scheme 6)

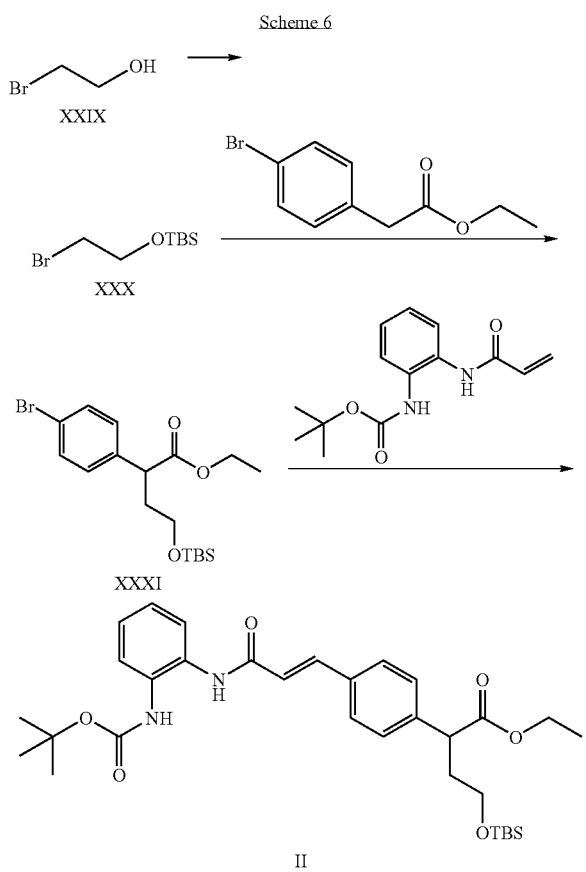

Key building block (E)-2-{4-[2-(2-tert-butoxycarbonylamino-phenylcarbamoyl)-vinyl]-phenyl}-4-(tert-butyl-dimethyl-silanyloxy)-butyric acid ethyl ester (II) can be prepared according to Scheme 6. Starting with commercially available 2-bromo-ethanol (XXIX), silylation with tert-butyldimethylsilyl chloride provides (2-bromo-ethoxy)-tert-butyl-dimethyl-silane (XXX). Alkylation of the potassium enolate of (4-bromo-phenyl)-acetic acid ethyl ester with XXX furnishes 2-(4-bromo-phenyl)-4-(tert-butyl-dimethyl-silanyloxy)-butyric acid ethyl ester (XXXI). Heck reaction of XXXI with (2-acryloylamino-phenyl)-carbamic acid tert-butyl ester gives key building block 2-{4-[2-(2-tert-butoxycarbonylamino-phenylcarbamoyl)-vinyl]-phenyl}-4-hydroxy-butyric acid ethyl ester (II).

2-Bromo-ethanol (XXIX) is commercially available.

(2-Bromo-ethoxy)-tert-butyl-dimethyl-silane (XXX) can be prepared from silylation of XXIX with tert-butyldimethylsilyl chloride. The reaction is typically performed by adding tert-butyldimethylsilyl chloride to a solution of XXIX in dimethylformamide and imidazole at room temperature for twelve hours.

2-(4-Bromo-phenyl)-4-(tert-butyl-dimethyl-silanyloxy)-butyric acid ethyl ester (XXXI) is prepared by alkylation of the corresponding potassium enolate with XXX. The reaction is typically carried out by deprotonating (4-bromo-phenyl)-acetic acid ethyl ester with potassium tert-butoxide in dimethylformamide at room temperature for one hour, then cooling the reaction to zero degrees Celsius and slowly adding XXX, followed by stirring at room temperature for twelve hours.

Key building block (E)-2-{4-[2-(2-tert-butoxycarbonylamino-phenylcarbamoyl)-vinyl]-phenyl}-4-(tert-butyl-dimethyl-silanyloxy)-butyric acid ethyl ester (II) can be prepared by Heck reaction of XXXI and (2-acryloylamino-phenyl)-carbamic acid tert-butyl ester. The reaction is typically performed in deoxygenated dimethylformamide with triethylamine, tri-ortho-tolyl-phosphine, $Pd_2(dba)_3$, at 90-110 degrees Celsius for about four to ten hours under inert atmosphere.

Synthesis of (E)-2-{4-[2-(2-tert-Butoxycarbonylamino-phenylcarbamoyl)-vinyl]-phenyl}-5-chloro-pentanoic acid methyl ester (scheme 7)

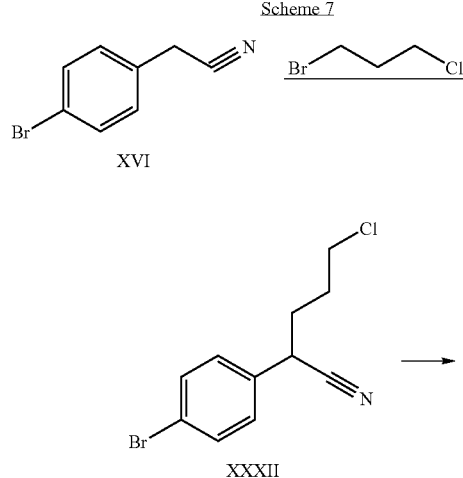

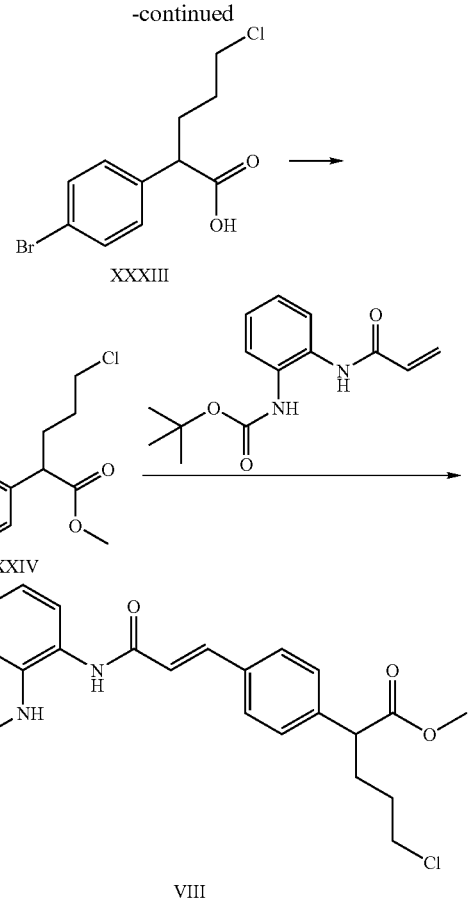

Key building block (E)-2-{4-[2-(2-tert-butoxycarbonylamino-phenylcarbamoyl)-vinyl]-phenyl}-5-chloro-pentanoic acid methyl ester (VIII) can be prepared according to Scheme 7. Starting with commercially available 4-(bromo-phenyl)-acetonitrile (XVI), deprotonation with strong base followed by alkylation using 1-bromo-3-chloropropane gives 2-(4-bromo-phenyl)-5-chloro-pentanenitrile (XXXII). Hydrolysis of XXXII under acidic conditions furnishes 2-(4-bromo-phenyl)-5-chloro-pentanoic acid (XXXIII). Nucleophilic acyl substitution converts XXXIII to 2-(4-bromo-phenyl)-5-chloro-pentanoic acid methyl ester (XXXIV), which undergoes Heck reaction with (2-acryloylamino-phenyl)-carbamic acid tert-butyl ester to give key building block (E)-2-{4-[2-(2-tert-butoxycarbonylamino-phenylcarbamoyl)-vinyl]-phenyl}-5-chloro-pentanoic acid methyl ester (VIII).

4-(Bromo-phenyl)-acetonitrile (XVI) is commercially available.

2-(4-bromo-phenyl)-5-chloro-pentanenitrile (XXXII) can be prepared by deprotonating XVI with a strong base, followed by alkylation with 1-bromo-3-chloropropane. The reaction is typically performed by dissolving XVI in a mixture of dimethylformamide and toluene, reaction with sodium hydride for one hour at zero degrees Celsius, and then addition of 1-bromo-3-chloropropane at ten degrees for 30 minutes.

2-(4-Bromo-phenyl)-5-chloro-pentanoic acid (XXXIII) can be prepared by acidic hydrolysis of XXXII. The reaction is carried out by refluxing XXXII in a mixture of concentrated sulfuric acid, glacial acetic acid, and water for twelve hours.

2-(4-Bromo-phenyl)-5-chloro-pentanoic acid methyl ester (XXXIV) can be prepared by nucleophilic acyl substitution of XXXIII with thionyl chloride in methanol. The reaction is typically performed by dissolving XXXIII in methanol at zero degrees Celsius, followed by addition of thionyl chloride and refluxing for five hours.

Key building block (E)-2-{4-[2-(2-tert-butoxycarbonylamino-phenylcarbamoyl)-vinyl]-phenyl}-5-chloro-pentanoic acid methyl ester (VIII) can be prepared by Heck reaction of XXXIV and (2-acryloylamino-phenyl)-carbamic acid tert-butyl ester. The reaction is typically performed in deoxygenated dimethylformamide with triethylamine, tri-ortho-tolyl-phosphine, Pd$_2$(dba)$_3$, at 90-110 degrees Celsius for about four to eight hours under inert atmosphere.

Synthesis of 2-(5-Bromo-pyridin-2-yl)-5-chloro-pentanoic acid (scheme 8)

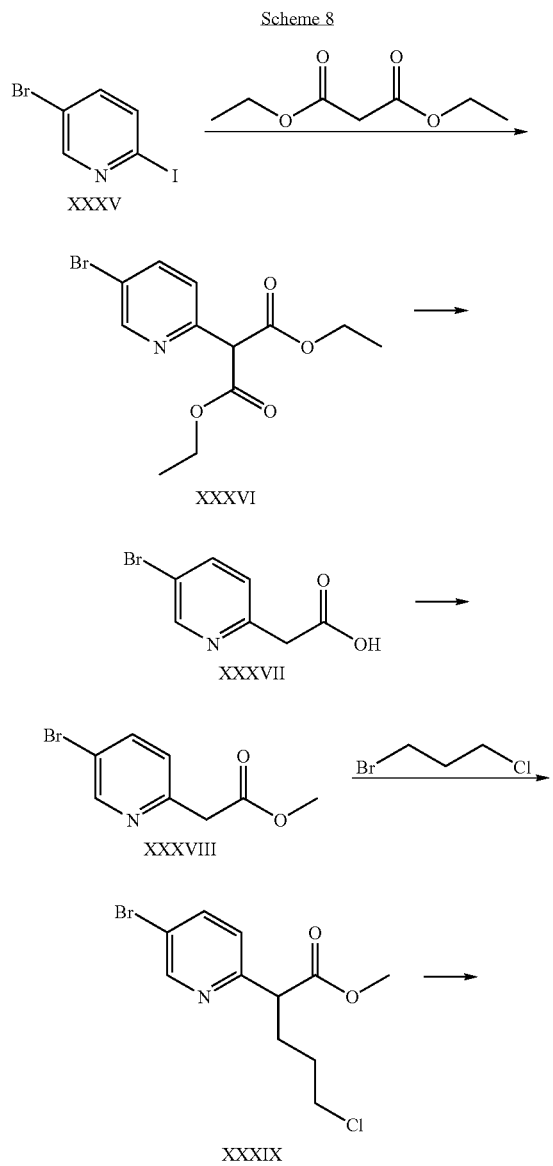

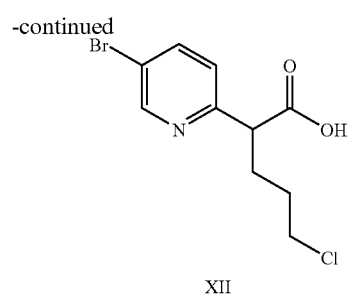

Key building block 2-(5-bromo-pyridin-2-yl)-5-chloro-pentanoic acid (XII) can be prepared according to Scheme 8. Starting with commercially available 5-bromo-2-iodo-pyridine (XXXV), copper-catalyzed reaction with malonic acid diethyl ester furnishes 2-(5-bromo-pyridin-2-yl)-malonic acid diethyl ester (XXXVI). Hydrolysis and decarboxylation under basic conditions gives (5-bromo-pyridin-2-yl)-acetic acid (XXXVII), which subsequently can undergo nucleophilic acyl substitution with thionyl chloride in methanol to provide (5-bromo-pyridin-2-yl)-acetic acid methyl ester (XXXVIII). Deprotonation of XXXVIII with strong base followed by alkylation with 1-bromo-3-chloropropane gives 2-(5-bromo-pyridin-2-yl)-5-chloro-pentanoic acid methyl ester (XXXIX), which can then be hydrolyzed under aqueous basic conditions to furnish key building block 2-(5-bromo-pyridin-2-yl)-5-chloro-pentanoic acid (XII).

5-Bromo-2-iodo-pyridine (XXXV) is commercially available.

2-(5-Bromo-pyridin-2-yl)-malonic acid diethyl ester (XXXVI) is prepared by copper-catalyzed reaction with malonic acid diethyl ester. The reaction is typically performed by mixing XXXV with malonic acid diethyl ester, copper iodide, cesium carbonate, and pyridine-2-carboxylic acid in 1,4-dioxane and heating to 70 degrees Celsius for 24 hours under nitrogen atmosphere.

(5-Bromo-pyridin-2-yl)-acetic acid (XXXVII) is prepared by basic hydrolysis and decarboxylation of XXXVI. The reaction is typically performed by dissolving XXXVII in methanol and adding aqueous sodium hydroxide, followed by reaction for three to four hours at room temperature.

(5-Bromo-pyridin-2-yl)-acetic acid methyl ester (XXXVIII) can be prepared by nucleophilic acyl substitution of XXXVII with thionyl chloride in methanol. The reaction is typically performed by dissolving XXXVII in methanol at zero degrees Celsius, followed by addition of thionyl chloride and reaction at room temperature for three hours.

2-(5-bromo-pyridin-2-yl)-5-chloro-pentanoic acid methyl ester (XXXIX) can be prepared by deprotonating XXXVIII with a strong base, followed by alkylation with 1-bromo-3-chloropropane. The reaction is typically performed by dissolving XXXVIII in dimethylformamide, reaction with sodium hydride for one hour at zero degrees Celsius, and then addition of 1-bromo-3-chloropropane at ten degrees for 30 minutes.

Key building block 2-(5-bromo-pyridin-2-yl)-5-chloro-pentanoic acid (XII) can be prepared by basic hydrolysis of XXXIX. The reaction is typically carried out by dissolving XXXIX in a mixture of tetrahydrofuran, methanol, and aqueous lithium hydroxide, and reacting for 16 hours at room temperature.

Each method for obtaining key building blocks according to schemes 6 to 8 as mentioned herein before is a further embodiment according to the present invention.

EXAMPLES

The following examples were prepared by the general methods outlined in the schemes above. They are intended to illustrate the meaning of the present invention but should by no means represent a limitation within the meaning of the present invention:

Example 1

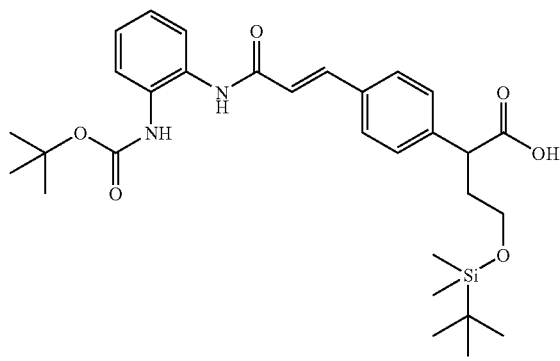

(E)-2-{4-[2-(2-tert-Butoxycarbonylamino-phenylcarbamoyl)-vinyl]-phenyl}-4-(tert-butyl-dimethyl-silanyloxy)-butyric acid To a solution of (E)-2-{4-[2-(2-tert-butoxycarbonylamino-phenylcarbamoyl)-vinyl]-phenyl}-4-(tert-butyl-dimethyl-silanyloxy)-butyric acid ethyl ester (2.63 g, 4.52 mmol) in MeOH/H$_2$O (30 mL/10 mL) was added LiOH.H$_2$O (556 mg, 13.56 mmol). This mixture was stirred for about 5 h at room temperature, and then evaporated to remove most of the MeOH. The aqueous layer was acidified with concentrated HCl to pH 5-6. The acidified aqueous layer was extracted with ethyl acetate (3×30 mL). The combined organic layer was washed with brine, dried with Na$_2$SO$_4$, filtered, and evaporated to obtain 2.0 g (80%) of a yellow solid product. MS: calc'd 555 (MH+), exp 555 (MH+).

Example 2

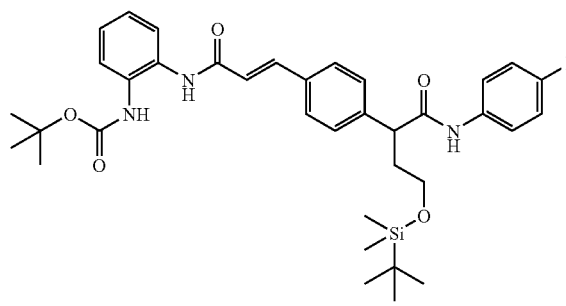

(E)-[2-(3-{4-[1-(4-Bromo-phenylcarbamoyl)-3-(tert-butyl-dimethyl-silanyloxy)-propyl]-phenyl}-acryloylamino)-phenyl]-carbamic acid tert-butyl ester To a solution of (E)-2-{4-[2-(2-tert-butoxycarbonylamino-phenylcarbamoyl)-vinyl]-phenyl}-4-(tert-butyl-dimethyl-silanyloxy)-butyric acid (2.5 g, 4.52 mmol), EDCI (1.2 g, 4.97 mmol) and HOBt (671 mg, 4.97 mol) in CH$_2$Cl$_2$ (50 mL) was added 4-bromo-phenylamine (786 mg, 4.57 mmol). This mixture was stirred overnight at room temperature and then diluted with CH$_2$Cl$_2$ (50 mL), washed with saturated aqueous NaHCO$_3$ solution, water and brine, dried with Na$_2$SO$_4$, and evaporated to obtain a yellow residue. MS: calc'd 708 (MH+), exp 708 (MH+).

Example 3

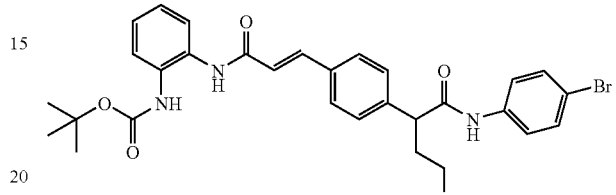

(E)-[2-(3-{4-[1-(4-Bromo-phenylcarbamoyl)-3-hydroxy-propyl]phenyl}-acryloylamino)-phenyl]carbamic acid tert-butyl ester To a solution of (E)-[2-(3-{4-[1-(4-bromo-phenylcarbamoyl)-3-(tert-butyl-dimethyl-silanyloxy)-propyl]-phenyl}-acryloylamino)-phenyl]-carbamic acid tert-butyl ester (1.6 g, 2.26 mmol) in THF (40 mL) was added tetrabutylammonium dihydrogen trifluoride (1.36 g, 4.52 mmol). This mixture was stirred at room temperature overnight and then evaporated to remove THF. The mixture was dissolved in water and extracted with ethyl acetate (3×30 mL). The combined organic layer was washed with brine, dried with Na$_2$SO$_4$, filtered, and evaporated. The crude product was purified by column chromatography (CH$_2$Cl$_2$:EtOAc=10:1) to get yellow solid product. MS: calc'd 594 (MH+), exp 594 (MH+).

Example 4

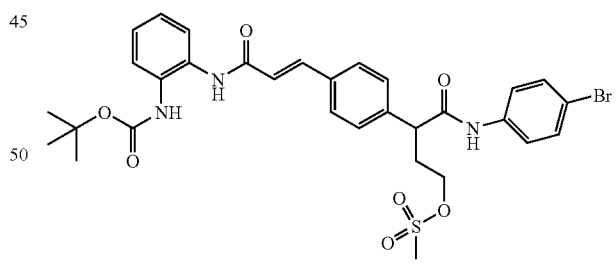

(E)-Methanesulfonic acid 3-(4-bromo-phenylcarbamoyl)-3-{4-[2-(2-tert-butoxycarbonylamino-phenylcarbamoyl)-vinyl]-phenyl}-propyl ester To a solution of (E)-[2-(3-{4-[1-(4-bromo-phenylcarbamoyl)-3-hydroxy-propyl]-phenyl}-cryloylamino)-phenyl]-carbamic acid tert-butyl ester (200 mg, 0.337 mmol) and DIPEA (81.6 mg, 0.674 mmol) in CH$_2$Cl$_2$ (10 mL) cooled to 0 degrees Celsius was added dropwise methanesulfonyl chloride (76.8 mg, 0.674 mmol) under N2 atmosphere. The reaction was stirred at 0 degrees Celsius until the starting material had been consumed according to TLC (about 1 hour). The mixture was diluted with CH$_2$Cl$_2$ (10 mL) and washed with water (10 mL) and brine (10 mL), dried with Na$_2$SO$_4$, filtered, and evaporated in vacuo to obtain 226 mg (quantitative yield) of light yellow solid which was used without further purification. MS: calc'd 672 (MH+), exp 672 (MH+).

Example 5

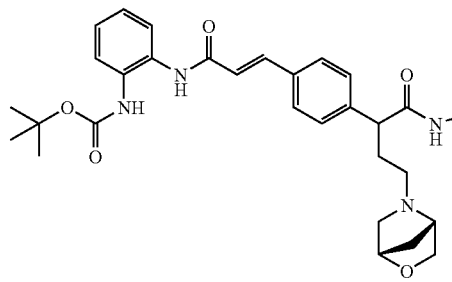

(E)-[2-(3-{4-[1-(4-Bromo-phenylcarbamoyl)-3-({1S,4S}-2-oxa-5-aza-bicyclo[2.2.1]hept-5-yl)-propyl]phenyl}-acryloylamino)-phenyl]-carbamic acid tert-butyl ester To a solution of (E)-methanesulfonic acid 3-(4-bromo-phenylcarbamoyl)-3-{4-[2-(2-tert-butoxycarbonylamino-phenylcarbamoyl)-vinyl]-phenyl}-propyl ester (226 mg, 0.337 mmol) and DIPEA (81.6 mg, 0.674 mmol) in CH$_2$Cl$_2$ (10 mL) was added (1S,4S)-2-oxa-5-aza-bicyclo[2.2.1]heptane (430 mg, 1.685 mmol). The reaction was stirred at room temperature overnight and diluted with CH$_2$Cl$_2$ (10 mL). The mixture was washed with water (10 mL) and brine (10 mL), dried with Na$_2$SO$_4$, filtered, and evaporated in vacuo to obtain light yellow solid which was used without further purification. MS: calc'd 675 (MH+), exp 675 (MH+).

Example 6

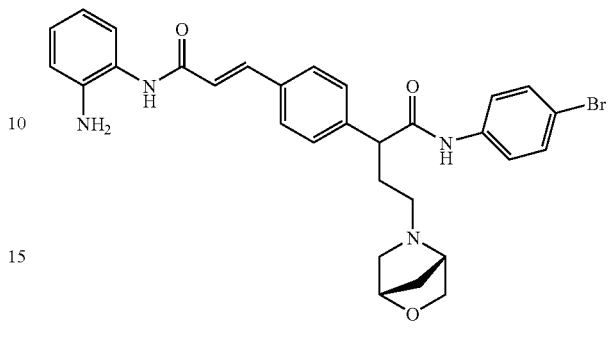

2-{4-[(E)-2-(2-Amino-phenylcarbamoyl)-vinyl]-phenyl}-N-(4-bromo-phenyl)-4-(1S,4S)-2-oxa-5-aza-bicyclo[2.2.1]hept-5-yl-butyramide Hydrochloric acid in methanol (1.25 M, 5 mL) was added to the (E)-[2-(3-{4-[1-(4-bromo-phenylcarbamoyl)-3-({1S,4S}-2-oxa-5-aza-bicyclo[2.2.1]hept-5-yl)-propyl]-phenyl}-acryloylamino)-phenyl]-carbamic acid tert-butyl ester residue, the mixture was stirred for about 4 h, and then NaHCO$_3$ was added to the reaction system. After filtration of solids, the crude mixture was purified by preparative HPLC to obtain light yellow solid. MS: calc'd 575 (MH+), exp 575 (MH+). $^1$H NMR (d$_6$-DMSO, 400 MHz), 10.25 (d, 1H, J=8.8 Hz), 9.40 (s, 1H), 7.59-7.45 (broad m, 9H), 7.39 (d, 1H, J=8.0 Hz), 6.94-6.85 (m, 2H), 6.75 (d, 1H, J=8.0 Hz), 6.58 (t, 1H, J=8.0 Hz), 4.95 (s, 1H), 4.31 (s, 1H), 3.85-3.78 (broad m, 2H), 3.47-3.42 (broad m, 2H), 2.78 (broad s, 1H), 2.43-2.20 (broad m, 3H), 1.78-1.54 (broad m, 3H).

The compounds described in the following tables were prepared by methods analogous to the synthetic methods described above, but using the appropriate starting materials.

TABLE 1

| Example # | Structure | MW | MS (MH+) calc'd | MS (MH+) exp |
|---|---|---|---|---|
| 6-2 | 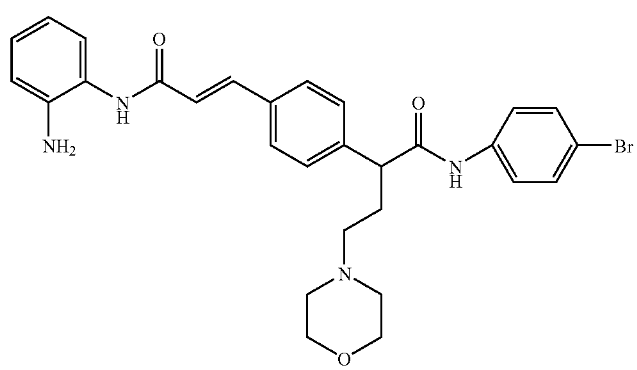 | 563.50 | 563 | 563 |

TABLE 1-continued

| Example # | Structure | MW | MS (MH+) calc'd | MS (MH+) exp |
|---|---|---|---|---|
| 6-3 | 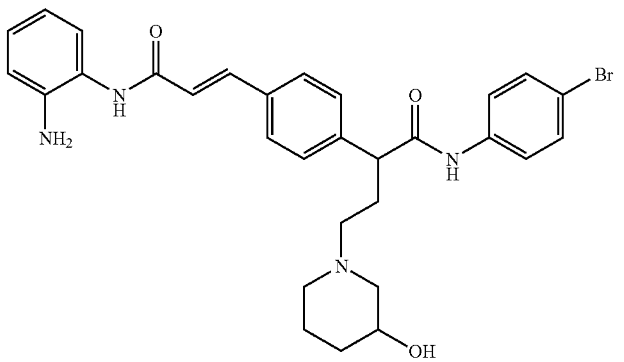 | 577.53 | 577 | 577 |

TABLE 2

| Example # | NMR data |
|---|---|
| 6-2 | ¹H NMR (d₄-MeOD, 400 MHz), 7.67 (d, 1H, J = 15.6 Hz), 7.62 (d, 2H, J = 8.4 Hz), 7.53-7.49 (m, 4H), 7.44 (d, 2H, J = 8.4 Hz), 7.22 (d, 1H, J = 7.6 Hz), 7.06 (t, 1H, J = 7.6 Hz), 6.89 (d, 1H, J = 8.4 Hz), 6.86 (d, 1H, J = 15.6 Hz), 6.76 (t, 1H, J = 7.6 Hz), 4.62 (s, 1H), 3.77 (broad s, 1H), 3.67 (t, 3H, J = 4.8 Hz), 3.37 (s, 1H), 2.47-2.41 (broad m, 6H), 1.97-1.95 (broad m, 1H). |
| 6-3 | ¹H NMR (d₆-DMSO, 400 MHz), 10.27 (s, 1H), 9.42 (s, 1H), 7.59-7.56 (m, 4H), 7.52 (d, 1H, J = 15.6 Hz), 7.47-7.44 (m, 4H), 7.33 (d, 1H, J = 7.6 Hz), 6.92 (t, 1H, J = 8.0 Hz), 6.87 (d, 1H, J = 15.6 Hz), 6.75 (d, 1H, J = 8.0 Hz), 6.58 (t, 1H, J = 7.6 Hz), 4.95 (s, 2H), 4.57 (s, 1H), 3.76 (d, 1H, J = 8.0 Hz), 2.78 (t, 1H, J = 10.6 Hz), 2.65-2.57 (m, 1H), 2.25 (broad s, 3H), 1.82-1.68 (broad m, 4H), 1.56 (broad s, 1H), 1.37-1.34 (m, 1H), 1.05-1.02 (m, 2H). |

Example 7

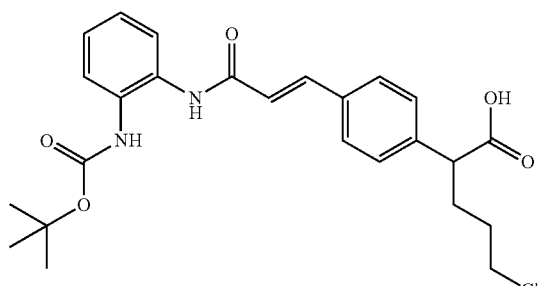

(E)-2-{4-[2-(-tert-Butoxycarbonylamino-phenylcarbamoyl)-vinyl]-phenyl}-5-chloro-pentanoic acid To a solution of (E)-2-{4-[2-(2-tert-butoxycarbonylaminophenylcarbamoyl)-vinyl]-phenyl}-5-chloro-pentanoic acid methyl ester (48.7 mg, 10 mmol) in MeOH/H₂O (4:1) (2 mL), LiOH (24 mg, 100 mmol) was added. After the solution was stirred at room temperature for 5 h, the solution was neutralized with 2N HCl to pH 5-6. The mixture was evaporated to dryness under reduced pressure, then EtOAc (10 mL) was added. The organic layer was washed with brine, dried with Na₂SO₄, filtered, and evaporated to obtain of a yellow solid product without further purification. MS: calc'd 473 (MH+), exp 473 (MH+). ¹H NMR (400 MHz, DMSO-d6) 12.50 (s, 1H), 9.73 (s, 1H), 8.50 (s, 1H), 6.89-7.64 (m, 10H), 3.61 (m, 3H), 1.55-2.10 (m, 4H), 1.46 (s, 9H).

Example 8

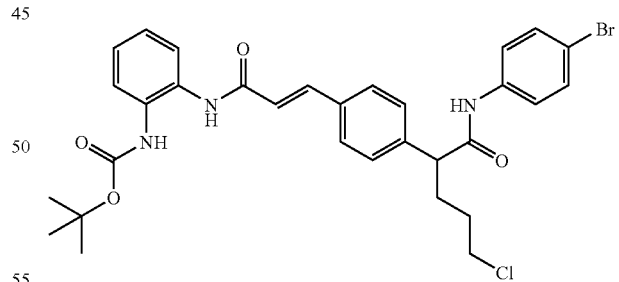

(E)-[2-(3-{4-[1-(4-Bromo-phenylcarbamoyl)-4-chloro-butyl]phenyl}-acryloylamino)-phenyl]-carbamic acid tert-butyl ester To a solution of (E)-2-{4-[2-tert-butoxycarbonylaminophenylcarbamoyl)-vinyl]-phenyl}-5-chloro-pentanoic acid (2.37 g, 5 mmol), DIPEA (1.21 g, 10 mmol), and Pybrop (4.66 g, 10 mmol) in CH₂Cl₂ (30 mL) was added 4-bromophenylamine (1.29 g, 7.5 mmol). This mixture was stirred overnight at room temperature and then evaporated. The mixture was redissolved in 40 mL of EtOAc and washed with 2N HCl (20 mL×3), brine, 5% NaHCO₃ (20 mL×3), brine, dried with Na₂SO₄, filtered and evaporated. The residue was purified by column chromatography on silica gel using hexane/EtOAc to give a white solid. MS: calc'd 626 (MH+), exp 626 (MH+).

Example 9

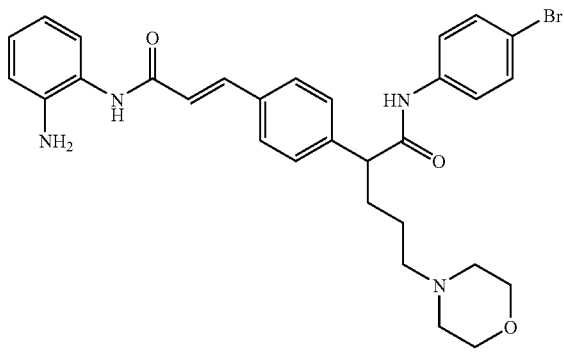

2-{4-[(E)-2-(2-Amino-phenylcarbamoyl)-vinyl]phenyl}-5-morpholin-4-yl-pentanoic acid (4-bromo-phenyl)-amide To a solution of (E)-[2-(3-{4-[1-(4-bromo-phenylcarbamoyl)-4-chloro-butyl]-phenyl}-acryloylamino)-phenyl]-carbamic acid tert-butyl ester (187.5 mg, 0.3 mmol) in DMF (3 mL), morpholine (261 mg, 3 mmol) was added. Then the solution was stirred at 80 degrees Celsius overnight. A solution of 1.25 M HCl/MeOH (4 mL) was added to the residue, the solution was stirred for 4 h at ambient temperature. After reaction, the solution was neutralized with solid NaHCO₃. The final product was obtained by preparative HPLC. MS: calc'd 577 (MH+), exp 577 (MH+). ¹H NMR (d₆-DMSO, 400 MHz), 10.33 (s, 1H), 9.57 (broad s, 2H), 7.61 (d, 1H, J=15.6 Hz), 7.59-7.54 (m, 4H), 7.49-7.46 (m, 4H), 7.36 (d, 1H, J=7.6 Hz), 6.99 (t, 1H, J=7.6 Hz), 6.91-6.84 (m, 2H), 6.71 (broad s, 1H), 3.96 (d, 2H, J=12.0 Hz,), 3.75 (t, 1H, J=7.2 Hz,), 3.62 (t, 2H, J=12.0 Hz), 3.40 (broad s, 2H), 3.14 (t, 2H, J=7.6 Hz), 3.03 (broad s, 2H), 2.09-2.04 (m, 1H), 1.78-1.71 (m, 1H), 1.67-1.57 (m, 2H).

The compounds described in the following tables were prepared by methods analogous to the synthetic methods described above, but using the appropriate starting materials.

TABLE 3

| Example # | Structure | MW | MS (MH+) calc'd | MS (MH+) exp |
|---|---|---|---|---|
| 9-2 | 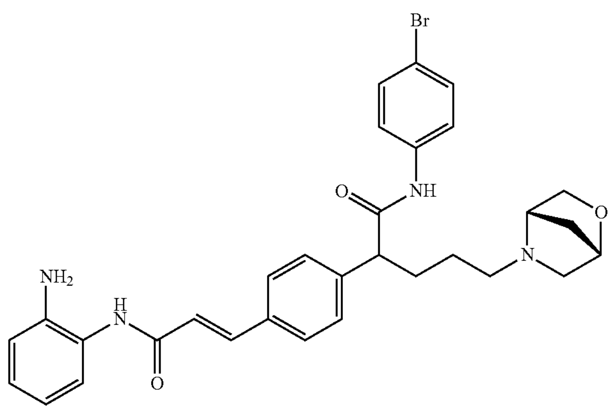 | 589.54 | 589 | 589 |
| 9-3 | 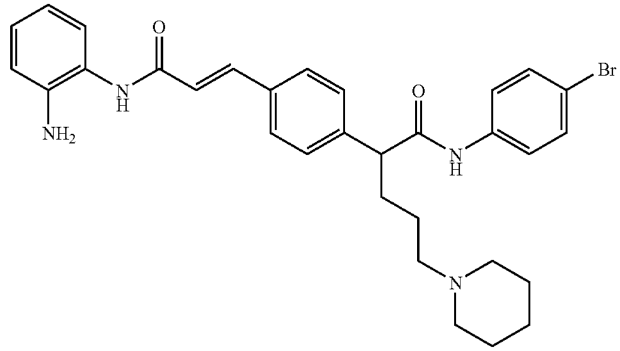 | 575.55 | 575 | 575 |

TABLE 3-continued

| Example # | Structure | MW | MS (MH+) calc'd | MS (MH+) exp |
|---|---|---|---|---|
| 9-4 | 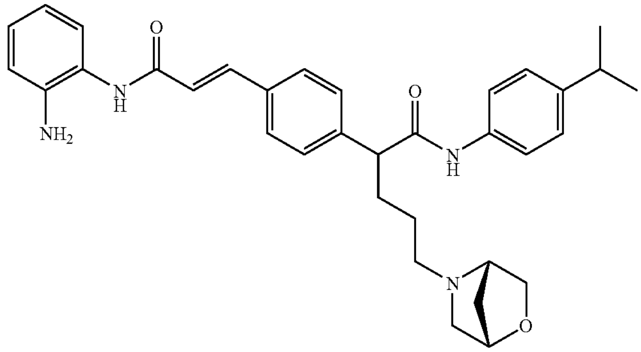 | 552.72 | 553 | 553 |
| 9-5 | 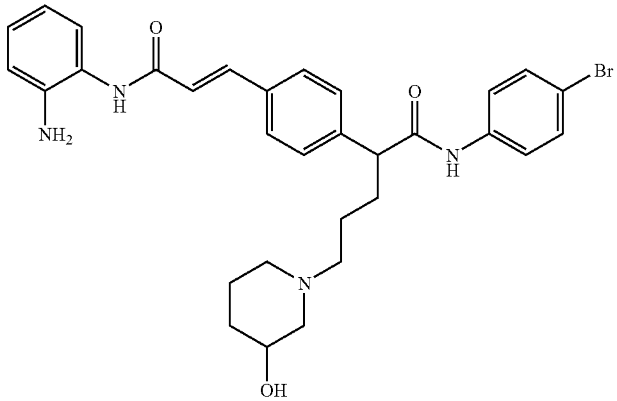 | 591.55 | 591 | 591 |
| 9-6 | 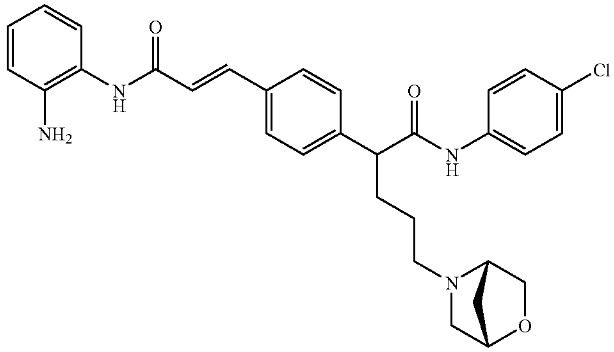 | 545.09 | 545 | 545 |
| 9-7 | 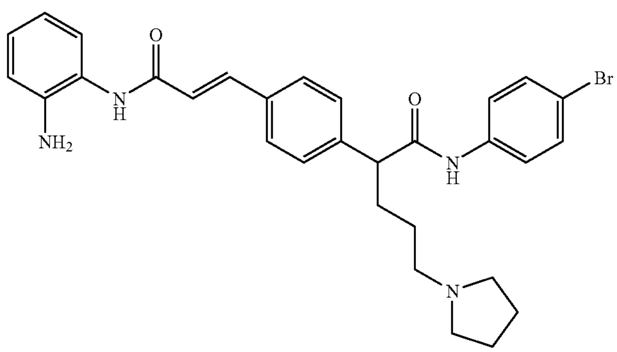 | 561.53 | 561 | 561 |

TABLE 3-continued

| Example # | Structure | MW | MS (MH+) calc'd | MS (MH+) exp |
|---|---|---|---|---|
| 9-8 | 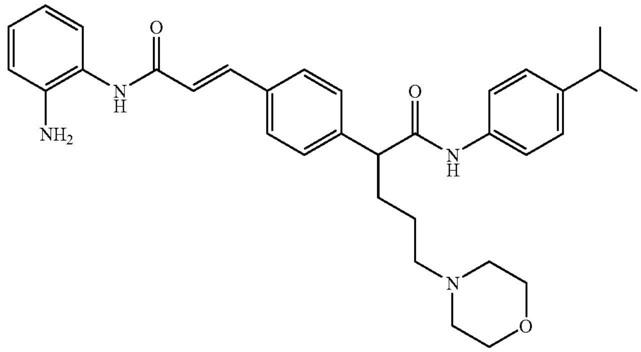 | 540.71 | 541 | 541 |
| 9-9 | 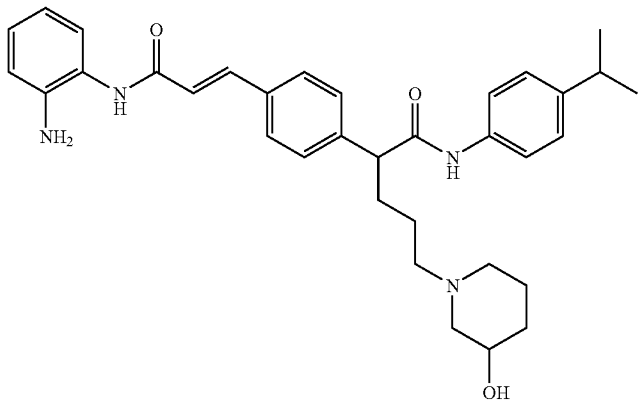 | 554.74 | 555 | 555 |
| 9-10 | 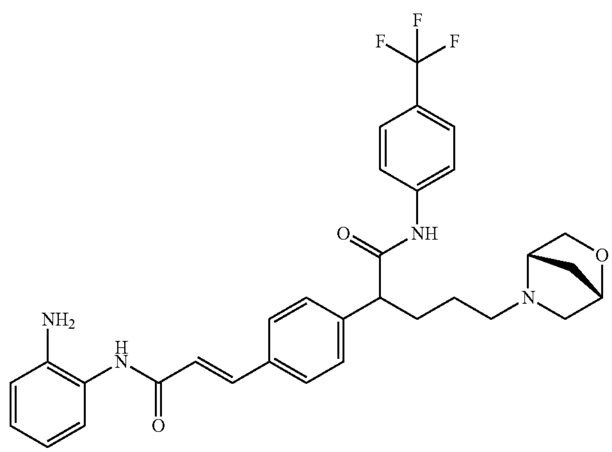 | 578.64 | 579 | 579 |
| 9-11 | 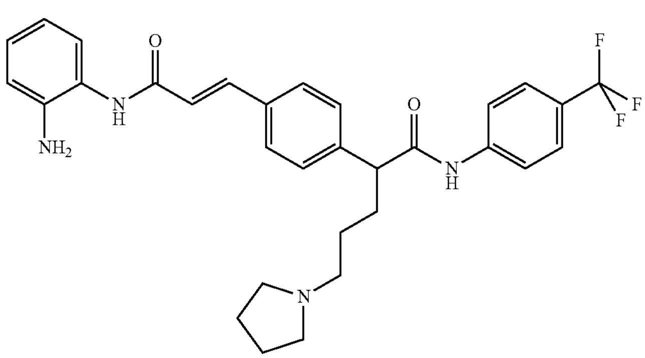 | 550.63 | 551 | 551 |

TABLE 3-continued

| Example # | Structure | MW | MS (MH+) calc'd | MS (MH+) exp |
|---|---|---|---|---|
| 9-12 | 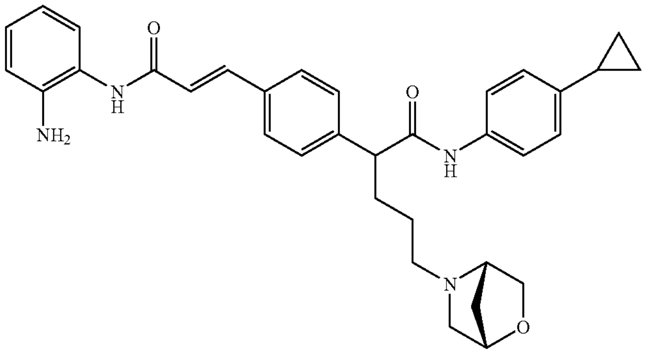 | 550.71 | 551 | 551 |
| 9-13 | 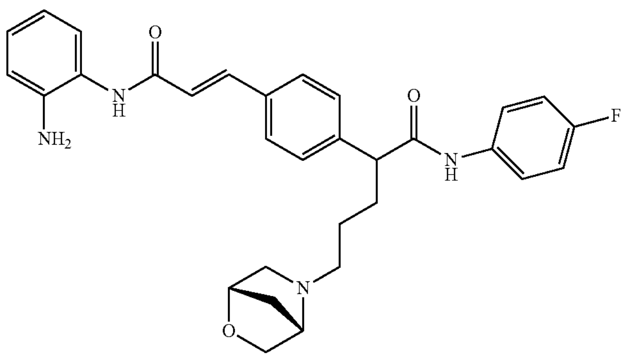 | 528.63 | 529 | 529 |
| 9-14 | 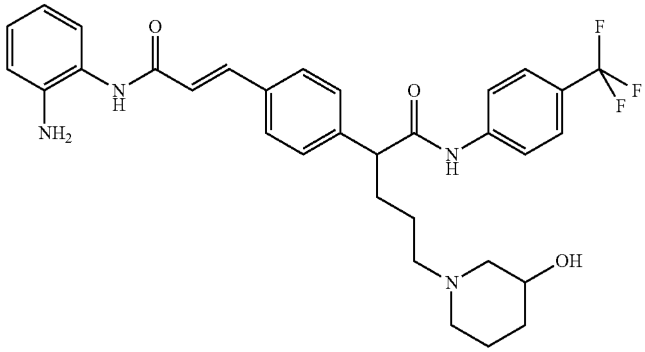 | 580.66 | 581 | 581 |
| 9-15 | 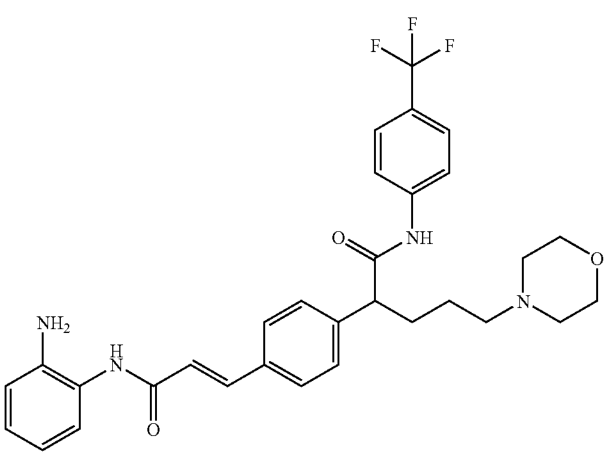 | 566.63 | 567 | 567 |

TABLE 3-continued

| Example # | Structure | MW | MS (MH+) calc'd | MS (MH+) exp |
|---|---|---|---|---|
| 9-16 | 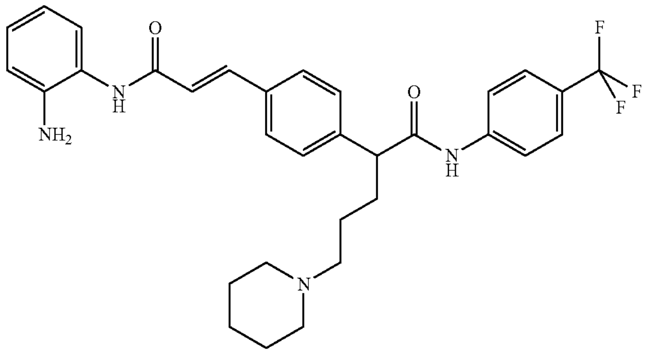 | 564.66 | 565 | 565 |
| 9-17 | 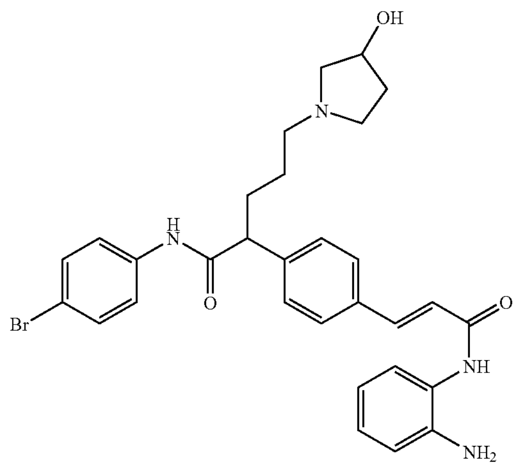 | 577.53 | 577 | 577 |
| 9-18 | 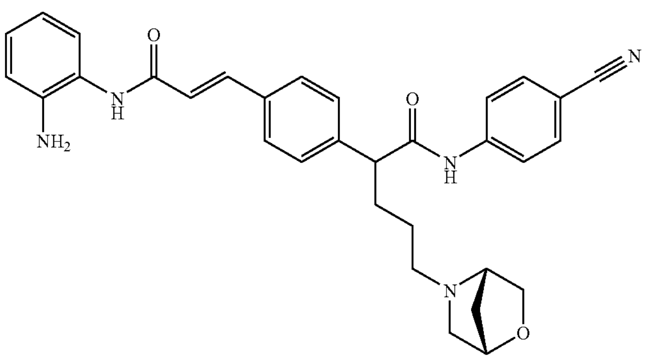 | 535.65 | 536 | 536 |
| 9-19 | 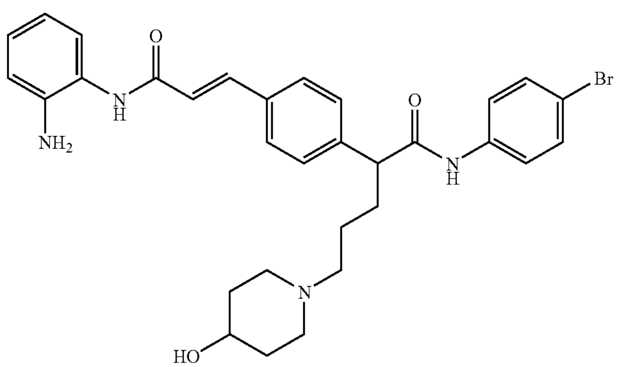 | 591.55 | 591 | 591 |

TABLE 4

| Example # | NMR data |
|---|---|
| 9-2 | $^1$H NMR (d$_6$-DMSO, 400 MHz), 10.28 (s, 1H), 9.42 (s, 1H), 7.60-7.56 (broad m, 4H), 7.52 (d, 1H, J = 15.6 Hz), 7.48-7.41 (m, 4H), 7.34 (d, 1H, J = 7.6 Hz), 6.93 (d, 1H, J = 8.0 Hz), 6.88 (d, 1H, J = 15.6 Hz), 6.75 (d, 1H, J = 8.0 Hz), 6.58 (t, 1H, J = 8.0 Hz), 4.95 (s, 2H), 4.28 (s, 1H), 3.79 (dd, 1H, J = 2.8, 7.6 Hz), 3.71 (t, 1H, J = 7.6 Hz), 3.45 (d, 1H, J = 6.8 Hz), 3.38 (d, 1H, J = 5.6 Hz), 2.71 (d, 1H, J = 9.6 Hz), 2.29 (dd, 1H, J = 2.8, 9.6 Hz), 2.10-2.05 (broad m, 1H), 1.78-1.73 (broad m, 1H), 1.67 (d, 1H, J = 9.6 Hz), 1.53 (d, 1H, J = 9.6 Hz), 1.35-1.30 (broad m, 2H). |
| 9-3 | $^1$H NMR (d$_4$-MeOD, 400 MHz), 7.76 (d, 1H, J = 15.6 Hz), 7.65 (d, 2H, J = 8.4 Hz), 7.54-7.52 (m, 4H), 7.45 (d, 2H, J = 8.4 Hz), 7.35-7.25 (broad m, 4H), 6.89 (d, 1H, J = 15.6 Hz), 3.78 (dd, 1H, J = 6.0, 8.4 Hz), 3.51 (d, 2H, J = 12.0 Hz), 3.13 (t, 2H, J = 7.6 Hz), 2.90 (t, 2H, J = 12.0 Hz), 2.22-2.19 (broad m, 1H), 1.96-1.68 (broad m, 8H), 1.55-1.49 (broad m, 1H). |
| 9-4 | $^1$H NMR (d$_6$-DMSO, 400 MHz), 7.71 (d, 1H, J = 15.6 Hz), 7.64 (d, 2H, J = 7.6 Hz), 7.54 (d, 2H, J = 8.0 Hz), 7.48 (d, 2H, J = 8.4 Hz), 7.25 (d, 1H, J = 7.6 Hz), 7.21 (d, 2H, J = 8.4 Hz), 7.10 (t, 1H, J = 7.6 Hz), 6.94-6.86 (m, 2H), 6.79 (t, 1H, J = 7.6 Hz), 4.43 (s, 1H), 4.04 (d, 1H, J = 7.6 Hz), 3.75 (t, 1H, J = 7.6 Hz), 3.64-3.60 (m, 2H), 2.96-2.84 (broad m, 2H), 2.81-2.63 (broad m, 2H), 2.60 (d, 1H, J = 10.6 Hz), 2.27-2.15 (broad m, 1H), 1.91 (d, 2H, J = 9.9 Hz), 1.78 (d, 1H, J = 9.9 Hz), 1.66-1.53 (broad m, 2H), 1.27 (s, 3H), 1.25 (s, 3H). |
| 9-5 | $^1$H NMR (d$_6$-DMSO, 400 MHz), 10.23 (broad s, 1H), 9.38 (broad s, 1H), 7.59-7.54 (m., 5H), 7.50-7.44 (m, 4H), 7.34 (d, 1H, J = 7.6 Hz), 6.93 (d, 1H, J = 7.2 Hz), 6.87 (d, 1H, J = 15.6 Hz), 6.76 (d, 1H, J = 7.2 Hz), 6.58 (t, 1H, J = 7.6 Hz), 4.93 (s, 2H), 4.53 (broad s, 1H), 3.71 (t, 1H, J = 7.6 Hz), 2.76 (d, 1H, J = 9.6 Hz), 2.57-2.54 (m, 1H), 2.27 (d, 2H, J = 5.2 Hz), 2.06-1.98 (broad m, 1H), 1.77-1.38 (broad m, 5H), 1.37-1.1.26 (broad m, 3H), 1.07-1.00 (m, 1H). |
| 9-6 | $^1$H NMR (d$_4$-MeOD, 400 MHz), 7.78 (d, 1H, J = 15.6 Hz), 7.66 (d, 2H, J = 7.6 Hz), 7.59-7.52 (m, 4H), 7.39 (s, 4H), 7.30 (d, 2H, J = 8.8 Hz), 6.89 (d, 1H, J = 15.6 Hz), 4.68 (broad s, 1H), 4.40 (broad s, 1H), 3.98 (broad s, 1H), 3.85-3.77 (m, 2H), 3.64 (broad s, 1H), 3.35-3.33 (s, 1H), 3.18-3.16 (m, 2H), 2.31-2.15 (broad m, 3H), 1.97-1.76 (m, 3H). |
| 9-7 | $^1$H NMR (d$_6$-DMSO, 400 MHz), 10.37 (s, 1H), 9.61 (s, 1H), 9.47 (broad s, 1H), 7.63-7.57 (m, 4H), 7.54-7.46 (m, 5H), 7.36 (d, 1H, J = 8.0 Hz), 6.99 (t, 1H, J = 8.0 Hz), 6.91-6.85 (m, 2H), 6.72 (t, 1H, J = 7.2 Hz), 3.75 (t, 1H, J = 7.2 Hz), 3.51 (broad s, 2H), 3.17-3.13 (m, 2H), 2.95 (broad s, 2H), 2.10-2.08 (m, 1H), 1.99 (broad s, 2H), 1.85-1.75 (m, 3H), 1.64-1.58 (m, 2H). |
| 9-8 | $^1$H NMR (d$_4$-MeOD, 400 MHz), 7.67 (d, 1H, J = 15.6 Hz), 7.62 (d, 2H, J = 8.0 Hz), 7.51 (d, 2H, J = 8.0 Hz), 7.44 (d, 2H, J = 8.0 Hz), 7.21 (d, 1H, J = 8.0 Hz), 7.18 (d, 2H, J = 8.8 Hz), 7.06 (d, 1H, J = 7.6 Hz), 6.89 (d, 1H, J = 8.8 Hz), 6.86 (d, 1H, J = 15.6 Hz), 6.76 (t, 1H, J = 7.6 Hz), 3.72-3.70 (m, 5H), 2.89-2.86 (m, 1H), 2.55-2.48 (m, 6H), 2.17 (broad s, 1H), 1.84 (broad s, 1H), 1.60 (broad s, 2H), 1.24 (s, 3H), 1.22 (s, 3H). |
| 9-9 | $^1$H NMR (d$_4$-MeOD, 400 MHz), 7.65 (d, 1H, J = 15.6 Hz), 7.58 (d, 2H, J = 8.0 Hz), 7.48 (d, 2H, J = 8.0 Hz), 7.42 (d, 2H, J = 8.4 Hz), 7.20 (d, 1H, J = 7.6 Hz), 7.15 (d, 2H, J = 8.4 Hz), 7.04 (t, 1H, J = 7.6 Hz), 6.87 (d, 1H, J = 8.0 Hz), 6.83 (d, 1H, J = 15.6 Hz), 6.74 (d, 1H, J = 7.6 Hz), 3.72-3.65 (m, 2H), 2.91-2.81 (m, 2H), 2.74-2.70 (m, 1H), 2.49-2.45 (m, 2H), 2.16-2.05 (broad m, 3H), 1.96-1.72 (broad m, 3H), 1.64-1.52 (m, 3H), 1.21 (s, 3H), 1.20 (s, 3H), 1.18 (broad s, 1H). |
| 9-10 | $^1$H NMR (d$_6$-DMSO, 400 MHz), 10.47 (s, 1H), 9.37 (s, 1H), 7.81 (d, 2H, J = 8.4 Hz), 7.66 (d, 2H, J = 8.4 Hz), 7.59 (d, 2H, J = 8.0 Hz), 7.53 (d, 1H, J = 15.6 Hz), 7.46 (d, 2H, J = 8.0 Hz), 7.34 (d, 1H, J = 7.6 Hz), 6.93 (d, 1H, J = 8.0 Hz), 6.88 (d, 1H, J = 15.6 Hz), 6.76 (d, 1H, J = 8.0 Hz), 6.58 (t, 1H, J = 7.6 Hz), 4.93 (s, 2H), 4.29 (s, 1H), 3.81-3.74 (m, 2H), 3.46 (d, 1H, J = 7.2 Hz), 3.39 (d, 1H, J = 5.6 Hz), 2.72 (d, 1H, J = 9.6 Hz), 2.31 (d, 1H, J = 9.6 Hz), 2.12-2.07 (m, 1H), 1.81-1.76 (m, 1H), 1.68 (d, 1H, J = 9.6 Hz), 1.53 (d, 1H, J = 9.6 Hz), 1.37-1.32 (m, 2H). |
| 9-11 | $^1$H NMR (d$_6$-DMSO, 400 MHz), 10.61 (s, 1H), 9.64 (s, 1H), 9.48 (broad s, 1H), 7.82 (d, 2H, J = 8.4 Hz), 7.68 (d, 2H, J = 8.4 Hz), 7.63 (d, 2H, J = 8.0 Hz), 7.56 (d, 1H, J = 15.6 Hz), 7.48 (d, 2H, J = 8.0 Hz), 7.36 (d, 1H, J = 8.0 Hz), 7.00 (t, 1H, J = 7.6 Hz), 6.91-6.87 (m, 2H), 6.75-6.74 (m, 1H), 3.82-3.78 (m, 2H), 3.18-3.16 (m, 3H), 2.96 (broad s, 2H), 2.12-2.10 (m, 1H), 1.99 (broad s, 2H), 1.85-1.75 (m, 3H) 1.61-1.59 (m, 2H). |

Example 10

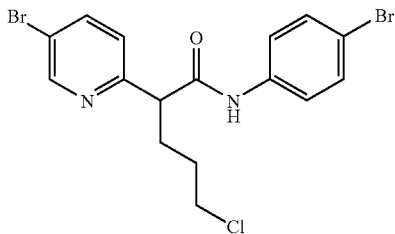

2-(5-Bromo-pyridin-2-yl)-5-chloro-pentanoic acid (4-bromo-phenyl)-amide

To a solution of 2-(5-Bromo-pyridin-2-yl)-5-chloro-pentanoic acid (1.9 g, 6.5 mmol), Et$_3$N (3.6 mL, 26 mmol), and Pybrop (6 g, 13 mmol) in CH$_2$Cl$_2$ (30 mL) was added 4-bromo-phenylamine (1.45 g, 8.45 mmol). This mixture was stirred overnight at room temperature and then evaporated. The mixture was redissolved in EtOAc (40 mL) and washed with 2N HCl (20 mL×3), brine, 5% NaHCO$_3$ (20 mL×3), brine, dried with Na$_2$SO$_4$, filtered and evaporated. The residue was purified by column chromatography on silica gel using hexane/EtOAc to give a white solid (1.63 g, 56% for two steps). MS: calc'd 444 (MH+), exp 444 (MH+). $^1$H NMR (400 MHz, CDCl$_3$-d) 9.65 (broad s, 1H), 8.72 (d, 1H, J=2.0 Hz), 8.06 (d, 1H, J=8.4 Hz), 7.53-7.41 (m, 4H), 4.18-4.08 (m, 1H), 3.66-3.54 (m, 2H), 2.45-2.35 (m, 1H), 2.21-2.11 (m, 1H), 1.98-1.87 (m, 1H), 1.83-1.72 (m, 1H).

Example 11

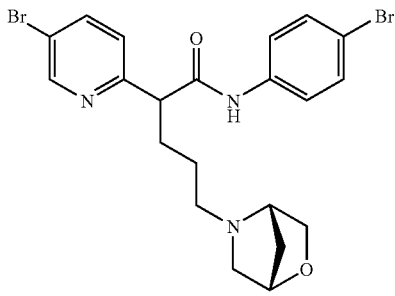

2-(5-Bromo-pyridi-2-yl)-5-({1S,4S}-2-oxa-5-aza-bicyclo[2.2.1]hept-5-yl)-pentanoic acid (4-bromo-phenyl)-amide To a mixture of 2-(5-Bromo-pyridin-2-yl)-5-chloro-pentanoic acid (4-bromo-phenyl)-amide (1.62 g, 3.63 mmol), Et$_3$N (2 mL, 14.52 mmol) in DMF (20 mL), (1S,4S)-2-oxa-5-aza-bicyclo[2.2.1]heptane (1.08 g, 10.89 mmol) was added. Then the solution was stirred at 80 degrees Celsius for 8 h. The mixture was redissolved in EtOAc (60 mL) and washed with water (20 mL×3), brine, dried with Na$_2$SO$_4$, filtered and evaporated. The residue was purified by column chromatography to give a white solid (1.28 g, 69%). MS: calc'd 508 (MH+), exp 508 (MH+).

Example 12

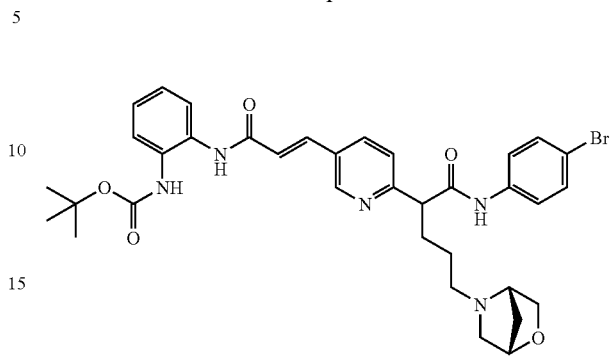

(E)-[2-(3-{6-[1-(4-Bromo-phenylcarbamoyl)-4-({1S, 4S}-2-oxa-5-aza-bicyclo[2.2.1]hept-5-yl)-butyl]-pyridin-3-yl}-acryloylamino)-phenyl]-carbamic acid tert-butyl ester A mixture of 2-(5-Bromo-pyridi-2-yl)-5-(2-oxa-5-aza-bicyclo[2.2.1]hept-5-yl)-pentanoic acid (4-bromo-phenyl)-amide (1.07 g, 2.1 mmol), (2-Acryloylamino-phenyl)-carbamic acid butyl ester (578 mg, 2.205 mmol), Pd$_2$(dba)$_3$ (385 mg, 0.42 mmol), tri-o-tolylphosphine (256 mg, 0.84 mmol) and triethylamine (636 mg, 6.3 mmol) in DMF (20 mL) was stirred at 80 degrees Celsius under N$^2$ for 15 h. The reaction mixture was diluted with EtOAc (80 mL), then washed with water (20 mL×2), brine (20 mL) and with Na$_2$SO$_4$. The solution was evaporated. The residue product was used directly without further purification. MS: calc'd 690 (MH+), exp 690 (MH+).

Example 13

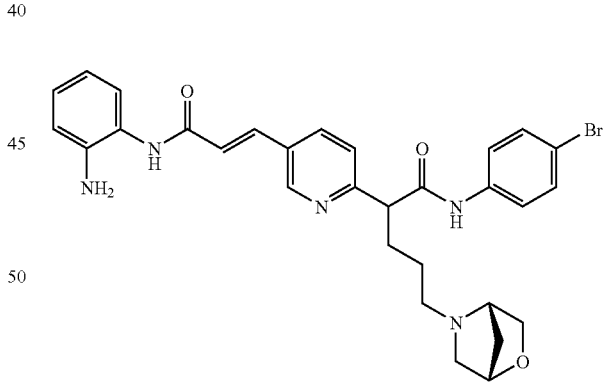

(E)-2-{5-[2-(2-Amino-phenylcarbamoyl)-vinyl]-pyridin-2-yl}-5-({1S,4S}-2-oxa-5-aza-bicyclo[2.2.1] hept-5-yl)-pentanoic acid (4-bromo-phenyl)-amide Hydrochloric acid in methanol (1.25 M, 5 mL) was added to the (E)-[2-(3-{6-[1-(4-Bromo-phenylcarbamoyl)-4-({1S, 4S}-2-oxa-5-aza-bicyclo[2.2.1]hept-5-yl)-butyl]-pyridin-3-yl}-acryloylamino)-phenyl]-carbamic acid tert-butyl ester residue, the mixture was stirred at room temperature for about 12 h, and then NaHCO$_3$ was added to the reaction system. After filtration of solids, the crude mixture was purified by preparative HPLC to obtain white solid. MS: calc'd 590 (MH+), exp 590 (MH+). $^1$H NMR (d$_4$-MeOD, 400 MHz), 8.76 (d, 1H, J=1.6 Hz), 8.09 (dd, 1H, J=2.0, 8.0 Hz), 7.70 (d, 1H, J=15.6 Hz), 7.61 (d, 1H, J=8.0 Hz), 7.57-7.52 (m, 2H), 7.48-7.43 (m, 2H), 7.21 (d, 1H, J=1.6 Hz), 7.10-7.04 (m, 1H), 6.97 (d, 1H, J=15.6 Hz), 6.90 (d, 1H, J=8.0 Hz), 6.77 (t, 1H, J=8.0 Hz), 4.46 (s, 1H), 4.02 (d, 1H, J=8.4 Hz), 3.95 (t, 1H, J=7.6 Hz), 3.76 (broad s, 1H), 3.66 (d, 1H, J=7.3 Hz), 2.95 (d, 1H, J=10.6 Hz), 2.87 (broad s, 1H), 2.77 (broad s, 2H), 2.24 (broad s, 1H), 2.03 (broad s, 1H), 1.95 (d, 1H, J=10.8 Hz), 1.85 (d, 1H, J=10.8 Hz), 1.63 (broad s, 2H).

Example 14

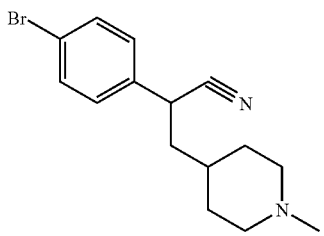

2-(4-Bromo-phenyl)-3-(1-methyl-piperidin-4-yl)-propionitrile

To a suspension of NaH (60%, 0.44 g, 11 mmol) dispersion in a mixture of DMF (6 mL)-toluene (12 mL), 4-bromobenzeneacetonitirle (1.96 g, 10 mmol) was added under N2. After stirring and cooling on ice for 1 h, 4-chloromethyl-1-methyl-piperidine (1.48 g, 10 mmol) was added dropwise. The mixture was stirred for 2 h under 70 degrees Celsius, then water was added and the mixture was extracted with EtOAc. The organic layer was dried (MgSO$_4$) and evaporated in vacuo to give an oily residue which was used without further purification. MS: calc'd 307 (MH+), exp 307 (MH+).

Example 15

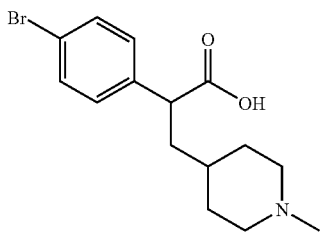

2-(4-Bromo-phenyl)-3-(1-methyl-piperidin-4-yl)-propionic acid

The oily residue of 2-(4-bromo-phenyl)-3-(1-methyl-piperidin-4-yl)-propionitrile was hydrolyzed by refluxing for 2 h with 4 mL of concentrated H$_2$SO$_4$ and water (38:28). The mixture was neutralized with Na$_2$CO$_3$, then MeOH (20 mL) was added. The solid was filtered and washed with MeOH (3×10 mL). The combined methanol solution was evaporated to give an oil. MS: calc'd 326 (MH+), exp 326 (MH+).

Example 16

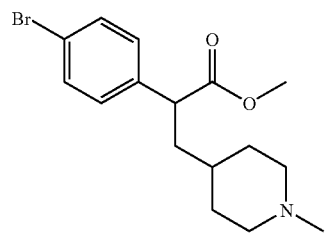

2-(4-Bromo-phenyl)-3-(1-methyl-piperidin-4-yl)-propionic acid methyl ester

To the solution of 2-(4-bromo-phenyl)-3-(1-methyl-piperidin-4-yl)-propionic acid in MeOH (60 mL), SOCl$_2$ (2 mL) was added at 0 degrees Celsius, then the mixture refluxed for 5 h. After cooling, the solution was evaporated to dryness under reduced pressure, then EtOAc was added, the organic layer was washed with aq. NaHCO$_3$, dried with MgSO$_4$, and evaporated to give an oil. MS: calc'd 340 (MH+), exp 340 (MH+).

Example 17

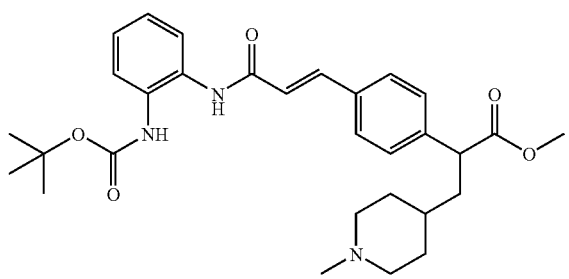

(E)-2-{4-[2-(2-tert-Butoxycarbonylamino-phenylcarbamoyl)-vinyl]-phenyl}-3-(1-methyl-piperidin-4-yl)-propionic acid methyl ester A mixture of 2-(4-bromo-phenyl)-3-(1-methyl-piperidin-4-yl)-propionic acid methyl ester (2.27 g, 6.67 mmol), (2-acryloylamino-phenyl)-carbamic acid tert-butyl ester (2 g, 7.2 mmol), Pd$_2$(dba)$_3$ (160 mg, 0.175 mmol), tri-o-tolylphosphine (160 mg, 0.526 mmol) and triethylamine (1.6 g, 15.8 mmol) in DMF (12 mL) was stirred at 100 degrees Celsius under N2 for 4 hours. After cooling to room temperature, the mixture was poured into a saturated aqueous solution of NH$_4$Cl, and extracted with ethyl acetate (80 mL). The organic layer was washed with brine, dried over Na$_2$SO$_4$, filtered, concentrated in vacuo, and purified by flash column chromatography to obtain a pale yellow solid (1.74 g, 50%). MS: calc'd 522 (MH+), exp 522 (MH+).

Example 18

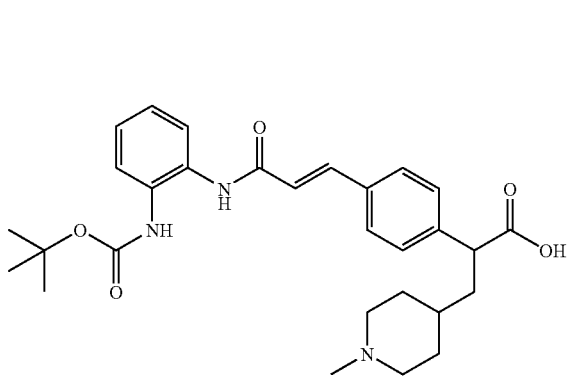

(E)-2-{4-[2-(2-tert-Butoxycarbonylamino-phenylcarbamoyl)-vinyl]-phenyl}-3-(1-methyl-piperidin-4-yl)-propionic acid To a solution of (E)-2-{4-[2-(2-tert-butoxycarbonylamino-phenylcarbamoyl)-vinyl]-phenyl}-3-(1-methyl-piperidin-4-yl)-propionic acid methyl ester (52.1 mg, 10 mmol) in MeOH/H$_2$O (4:1) (2 mL), LiOH (24 mg, 100 mmol.) was added. After the solution was stirred at room temperature for 5 h, the solution was neutralized with 2N HCl to pH 5-6. The mixture was evaporated to dryness under reduced pressure, then EtOAc (10 mL) was added. The organic layer was washed with brine, dried with Na$_2$SO$_4$, filtered, and evaporated to obtain a yellow solid product without further purification. MS: calc'd 508 (MH+), exp 508 (MH+).

Example 19

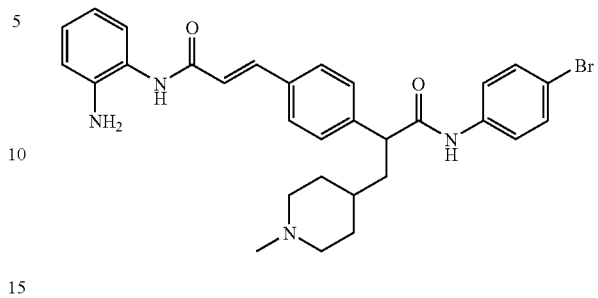

(E)-N-(2-Amino-phenyl)-3-{4-[1-(4-bromo-phenylcarbamoyl)-2-(1-methyl-piperidin-4-yl)-ethyl]phenyl}-acrylamide To a solution of (E)-2-{4-[2-(2-tert-butoxycarbonylamino-phenylcarbamoyl)-vinyl]-phenyl}-3-(1-methyl-piperidin-4-yl)-propionic acid (2.54 g, 5 mmol), Et$_3$N (1.21 g, 10 mmol), and HATU (3.80 g, 10 mmol) in CH$_2$Cl$_2$ (30 mL) was added 4-bromo-phenylamine (1.29 g, 7.5 mmol). This mixture was stirred overnight at room temperature and then evaporated. The mixture was redissolved in 20 ml of EtOAc and washed with 2N HCl (20 mL×3), brine, 5% NaHCO$_3$ (20 mL×3), brine, dried with Na$_2$SO$_4$, filtered and evaporated. The residue was purified by column chromatography on silica gel using hexane/EtOAc to give a white solid. 1.25 M HCl/MeOH (4 mL) was added to the product. The solution was stirred for 4 h at ambient temperature. After reaction, the solution was neutralized with solid NaHCO$_3$. The final product was obtained by preparative HPLC. MS: calc'd 561 (MH+), exp 561 (MH+). $^1$H NMR (d$_6$-DMSO, 400 MHz), 10.29 (s, 1H), 9.40 (s, 1H), 7.60-7.51 (m, 5H), 7.49-7.45 (m, 4H), 7.34 (d, 1H, J=7.6 Hz), 6.94-6.85 (m, 2H), 6.75 (d, 1H, J=7.6 Hz), 6.58 (t, 1H, J=7.6 Hz), 4.94 (broad s, 2H), 3.84 (t, 1H, J=7.6 Hz), 2.97 (broad s, 2H), 2.36 (s, 3H), 2.22 (broad s, 2H), 2.07-2.00 (m, 1H), 1.80-1.63 (m, 3H), 1.30-1.24 (m, 3H).

The compounds described in the following table 5 were prepared by methods analogous to the synthetic methods described in example 19 above, but using the appropriate starting materials.

TABLE 5

| Example # | Structure | MW | MS (MH+) calc'd | MS (MH+) exp |
|---|---|---|---|---|
| 19-2 | 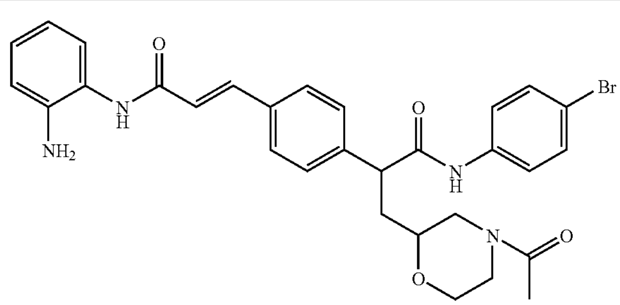 | 591.51 | 591 | 591 |

TABLE 5-continued

| Example # | Structure | MW | MS (MH+) calc'd | MS (MH+) exp |
|---|---|---|---|---|
| 19-3 | 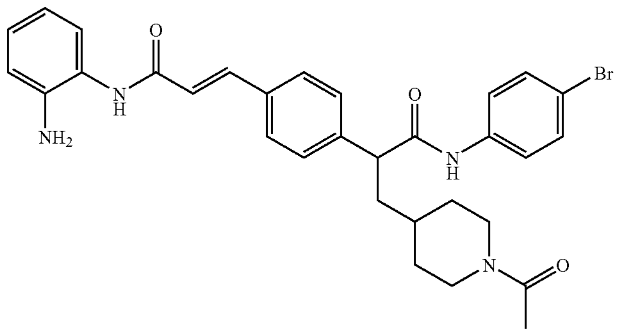 | 589.54 | 589 | 589 |
| 19-4 | 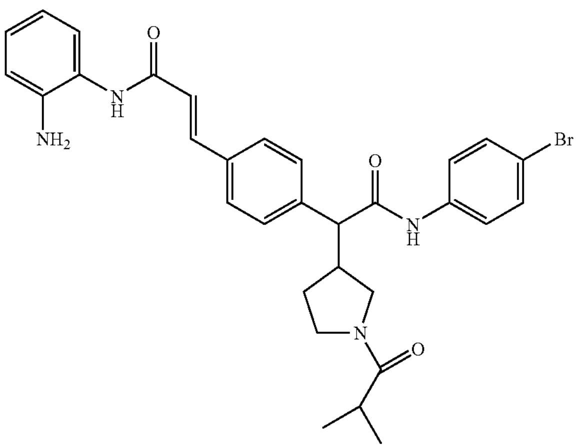 | 589.54 | 589 | 589 |
| 19-5 | 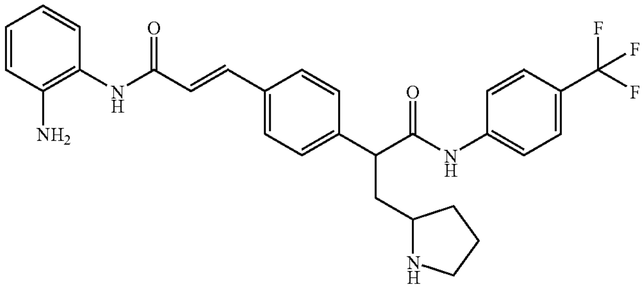 | 522.58 | 523 | 523 |
| 19-6 | 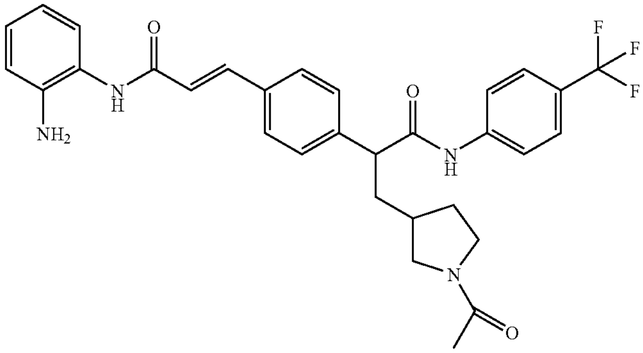 | 564.61 | 565 | 565 |

TABLE 5-continued

| Example # | Structure | MW | MS (MH+) calc'd | MS (MH+) exp |
|---|---|---|---|---|
| 19-7 | 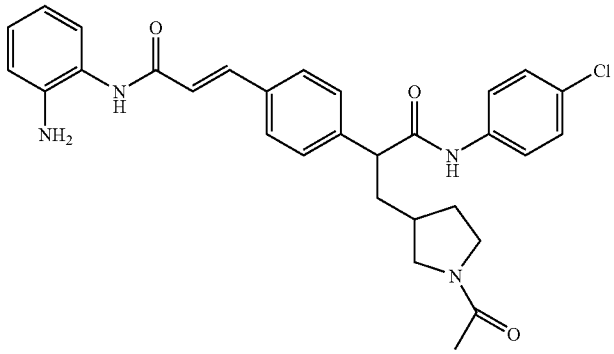 | 531.06 | 531 | 531 |
| 19-8 | 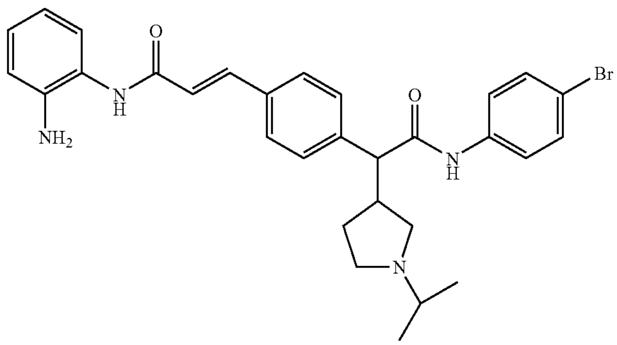 | 561.53 | 561 | 561 |
| 19-9 | 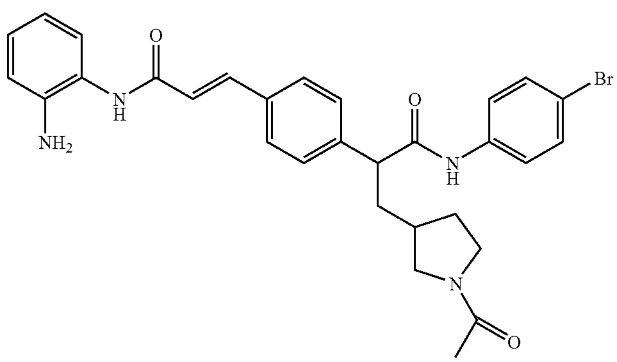 | 575.51 | 575 | 575 |
| 19-10 | 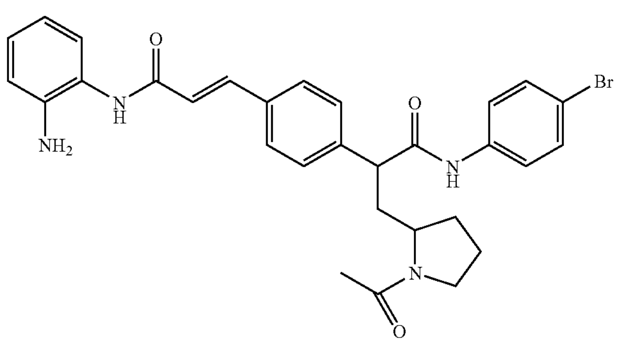 | 575.51 | 575 | 575 |

Example 20

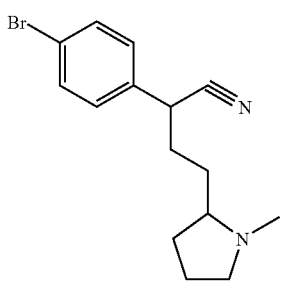

2-(4-Bromo-phenyl)-4-(1-methyl-pyrrolidin-2-yl)-butyronitrile

To a suspension of NaH (60%, 0.44 g, 11 mmol) dispersion in a mixture of DMF (6 mL)-toluene (12 mL), 4-bromobenzeneacetonitirle (1.96 g, 10 mmol) was added under N2. After stirring and cooling on ice for 1 h, 2-(2-chloro-ethyl)-1-methyl-pyrrolidine (1.48 g, 10 mmol) was added dropwise. The mixture was stirred for 2 h at 70 degrees Celsius, then water was added and the mixture was extracted with EtOAc. The organic layer was dried (MgSO$_4$) and evaporated in vacuo to give an oily residue which was used without further purification. MS: calc'd 307 (MH+), exp 307 (MH+).

Example 21

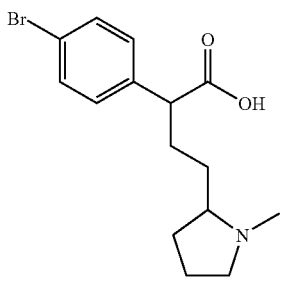

2-(4-Bromo-phenyl)-4-(1-methyl-pyrrolidin-2-yl)-butyric acid

The oily residue of 2-(4-bromo-phenyl)-4-(1-methyl-pyrrolidin-2-yl)-butyronitrile was hydrolyzed by refluxing for 2 h with concentrated H$_2$SO$_4$ and water (38:28) (4 mL). The mixture was neutralized with Na$_2$CO$_3$, then MeOH (20 mL) was added. The solid was filtered and washed with MeOH (3×10 mL). The combined methanol solution was evaporated to give an oil product. MS: calc'd 326 (MH+), exp 326 (MH+).

Example 22

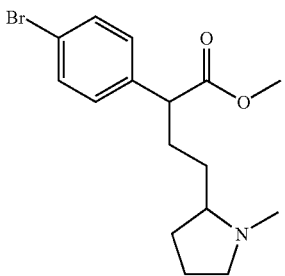

2-(4-Bromo-phenyl)-4-(1-methyl-pyrrolidin-2-yl)-butyric acid methyl ester

To the solution of 2-(4-bromo-phenyl)-4-(1-methyl-pyrrolidin-2-yl)-butyric acid in MeOH (60 mL), SOCl$_2$ (2 mL) was added at 0 degrees Celsius, then the mixture refluxed for 5 h. After cooling, the solution was evaporated to dryness under reduced pressure, then EtOAc was added, the organic layer was washed with aq. NaHCO$_3$, dried with MgSO$_4$, and evaporated to give an oil. MS: calc'd 340 (MH+), exp 340 (MH+).

Example 23

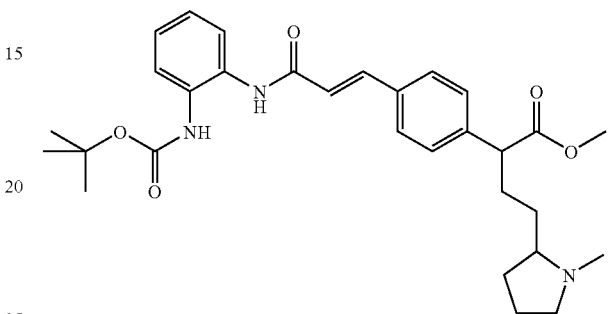

(E)-2-{4-[2-(2-tert-Butoxycarbonylamino-phenylcarbamoyl)-vinyl]-phenyl}-4-(1-methyl-pyrrolidin-2-yl)-butyric acid methyl ester A mixture of 2-(4-bromo-phenyl)-4-(1-methyl-pyrrolidin-2-yl)-butyric acid methyl ester (2.27 g, 6.67 mmol), (2-acryloylamino-phenyl)-carbamic acid tert-butyl ester (2 g, 7.2 mmol), Pd$_2$(dba)$_3$ (160 mg, 0.175 mmol), tri-o-tolylphosphine (160 mg, 0.526 mmol) and triethylamine (1.6 g, 15.8 mmol) in DMF (12 mL) was stirred at 100 degrees Celsius under N2 for 4 hours. After cooling to room temperature, the mixture was poured into a saturated aqueous solution of NH$_4$Cl, and extracted with ethyl acetate (80 mL). The organic layer was washed with brine, dried over Na$_2$SO$_4$, filtered, concentrated in vacuo, and purified by flash column chromatography to obtain pale yellow solid. (1.74 g, 50%). MS: calc'd 522 (MH+), exp 522 (MH+).

Example 24

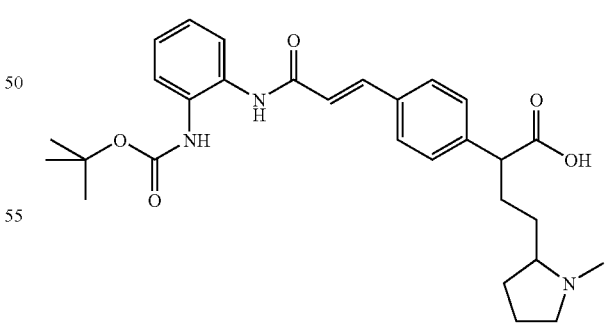

(E)-2-{4-[2-(2-tert-Butoxycarbonylamino-phenylcarbamoyl)-vinyl]phenyl}-4-(1-methyl-pyrrolidin-2-yl)-butyric acid To a solution of (E)-2-{4-[2-(2-tert-butoxycarbonylamino-phenylcarbamoyl)-vinyl]-phenyl}-4-(1-methyl-pyrrolidin- 2-yl)-butyric acid methyl ester (52.1 mg, 10 mmol) in MeOH/H₂O (4:1) (2 mL), LiOH (24 mg, 100 mmol.) was added. After the solution was stirred at room temperature for 5 h, the solution was neutralized with 2N HCl to pH 5-6. The mixture was evaporated to dryness under reduced pressure, then EtOAc (10 mL) was added. The organic layer was washed with brine, dried with Na₂SO₄, filtered, and evaporated to obtain a yellow solid product without further purification. MS: calc'd 508 (MH+), exp 508 (MH+).

Example 25

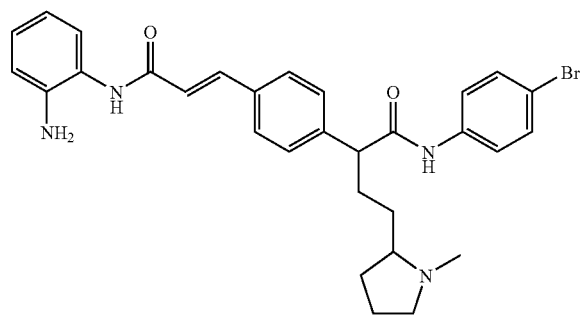

2-{4-[(E)-2-(2-Amino-phenylcarbamoyl)-vinyl]-phenyl}-N-(4-bromo-phenyl)-4-(1-methyl-pyrrolidin-2-yl)-butyramide To a solution of (E)-2-{4-[2-(2-tert-butoxycarbonylamino-phenylcarbamoyl)-vinyl]-phenyl}-4-(1-methyl-pyrrolidin-2-yl)-butyric acid (2.54 g, 5 mmol), Et₃N (1.21 g, 10 mmol), and HATU (3.80 g, 10 mmol) in CH₂Cl₂ (30 mL) was added 4-bromo-phenylamine (1.29 g, 7.5 mmol). This mixture was stirred overnight at room temperature and then evaporated. The mixture redissolved in 20 mL of EtOAc and washed with 2N HCl (20 mL×3), brine, 5% NaHCO₃ (20 mL×3), brine, dried with Na₂SO₄, filtered and evaporated. The residue was purified by column chromatography on silica gel using hexane/EtOAc to give a white solid. 1.25 M HCl/MeOH (4 mL) was added to the product. The solution was stirred for 4 h at ambient temperature. After reaction, the solution was neutralized with solid NaHCO₃. The final product was obtained by preparative HPLC. MS: calc'd 561 (MH+), exp 561 (MH+).
¹H NMR (d₆-DMSO, 400 MHz), 10.25 (d, 1H, J=8.8 Hz), 9.40 (s, 1H), 7.60-7.56 (m, 4H), 7.53 (d, 1H, J=15.6 Hz), 7.49-7.45 (m, 4H), 7.34 (d, 1H, J=8.0 Hz), 6.93 (d, 1H, J=7.6 Hz), 6.88 (d, 1H, J=15.6 Hz), 6.75 (d, 1H, J=7.6 Hz), 6.58 (t, 1H, J=8.0 Hz), 4.95 (s, 2H), 3.71 (broad s, 1H), 3.07 (broad s, 1H), 2.31 (broad s, 4H), 1.99 (broad s, 2H), 1.69-1.46 (broad m, 5H).

Example 26

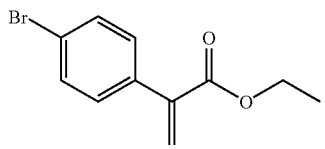

2-(4-Bromo-phenyl)-acrylic acid ethyl ester

To a solution of (4-bromo-phenyl)-acetic acid ethyl ester (972.4 mg, 4 mmol), paraformaldehyde (240 mg, 8 mmol), and Bu₄NCl (22 mg, 0.08 mmol) in DMF (10 mL) was added K₂CO₃ (1.32 g, 9.6 mmol). This mixture was heated at 60 degrees Celsius for 2 h. Then the mixture was cooled and diluted with EtOAc (30 mL) and washed with water (20 mL×3), brine, dried over Na₂SO₄, filtered and evaporated. The residue was purified by flash column chromatography on silica gel to give a white solid (0.74 g, 73%). MS: calc'd 255 (MH+), exp 255 (MH+).

Example 27

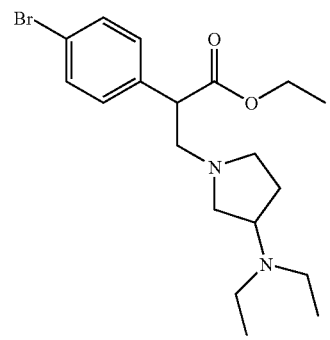

2-(4-Bromo-phenyl)-3-(3-diethylamino-pyrrolidin-1-yl)-propionic acid ethyl ester To a solution of diethyl-pyrrolidin-3-yl-amine (0.685 g, 6 mmol) in THF (10 mL) was added 2-(4-bromo-phenyl)-acrylic acid ethyl ester (1.27 g, 5 mmol) dropwise in THF at 0 degrees Celsius. Then the mixture was stirred at room temperature for 1 h and concentrated in vacuo. The residue was dissolved in EtOAc (30 mL), washed with water (20 mL×2), brine, dried over Na₂SO₄, filtered and evaporated. The obtained oil was used directly without further purification. MS: calc'd 397 (MH+), exp 397 (MH+).

Example 28

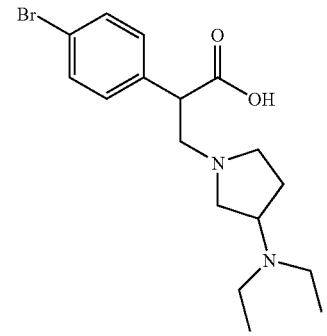

2-(4-Bromo-phenyl)-3-(3-diethylamino-pyrrolidin-1-yl)-propionic acid

To a solution of 2-(4-bromo-phenyl)-3-(3-diethylamino-pyrrolidin-1-yl)-propionic acid ethyl ester (639 mg, 1.6 mmol) in MeOH (4 mL) was added aq. NaOH (2N, 8 mmol). The solution was stirred at 40 degrees Celsius for 2 h, then concentrated in vacuo. The residue was dissolved in water and neutralized with 2N HCl to pH 5-6 at 0 degrees Celsius. Then the mixture was evaporated to dryness under reduced pressure to obtain a white solid product without further purification. MS: calc'd 369 (MH+), exp 369 (MH+).

Example 29

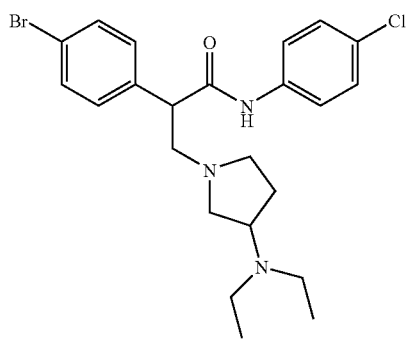

2-(4-Bromo-phenyl)-N-(4-chloro-phenyl)-3-(diethylamino-pyrrolidin-1-yl)-propionamide To a solution of 2-(4-bromo-phenyl)-3-(3-diethylamino-pyrrolidin-1-yl)-propionic acid (590 mg, 1.6 mmol), DIPEA (1.03 g, 8 mmol), and Pybrop (1.12 g, 2.4 mmol) in $CH_2Cl_2$ (10 mL) was added 4-chloro-phenylamine (306 mg, 2.4 mmol). This mixture was stirred overnight at room temperature and then evaporated. The mixture redissolved in EtOAc (20 mL) and washed with water, brine, dried with $Na_2SO_4$, concentrated in vacuo. The residue was purified by flash column chromatography to give a white solid. MS: calc'd 478 (MH+), exp 478 (MH+).

Example 30

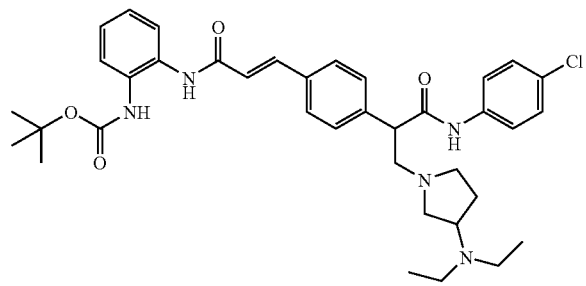

(E)-[2-(3-{4-[1-(4-Chloro-phenylcarbamoyl)-2-(3-diethylamino-pyrrolidin-1-yl)-ethyl]-phenyl}-acryloylamino)-phenyl]-carbamic acid tert-butyl ester A mixture of 2-(4-bromo-phenyl)-N-(4-chloro-phenyl)-3-(diethylamino-pyrrolidin-1-yl)-propionamide (826 mg, 1.72 mmol), (2-acryloylamino-phenyl)-carbamic acid tert-butyl ester (452 mg, 1.72 mmol), $Pd_2(dba)_3$ (47.3 mg, 0.051 mmol), tri-o-tolylphosphine (62.8 mg, 0.017 mmol) and triethylamine (694 mg, 6.88 mmol) in DMF (10 mL) was stirred at 100 degrees Celsius under N2 for 4 hours. After cooling to room temperature, the mixture was poured into a saturated aqueous solution of $NH_4Cl$, and extracted with EtOAc (80 mL). The organic layer was washed with brine, dried over $Na_2SO_4$, filtered, concentrated in vacuo, and used directly without further purification. MS: calc'd 660 (MH+), exp 660 (MH+).

Example 31

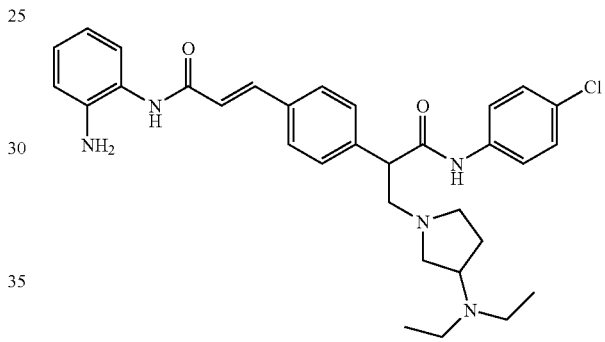

(E)-N-(2-Amino-phenyl)-3-{4-[1-(4-chloro-phenylcarbamoyl)-2-(3-diethylamino-pyrrolidin-1-yl)-ethyl]phenyl}-acrylamide To a solution of (E)-[2-(3-{4-[1-(4-chloro-phenylcarbamoyl)-2-(3-diethylamino-pyrrolidin-1-yl)-ethyl]-phenyl}-acryloylamino)-phenyl]-carbamic acid tert-butyl ester (528 mg, 0.8 mmol) in $CH_2Cl_2$ (10 mL) was added $CF_3COOH$ (612 uL, 8 mmol). The mixture was stirred for about 4 h, and then $NaHCO_3$ was added to the reaction system. After filtration of solids, the crude mixture was purified by preparative HPLC to obtain a light yellow solid. MS: calc'd 560 (MH+), exp 560 (MH+). $^1$H NMR ($d_4$-MeOD, 400 MHz), 7.66 (d, 1H, J=15.6 Hz), 7.60-7.57 (m, 4H), 7.49 (d, 2H, J=8.0 Hz), 7.29 (d, 2H, J=8.8 Hz), 7.22 (d, 1H, J=7.6 Hz), 7.06 (t, 1H, J=7.6 Hz), 6.89 (d, 1H, J=8.8 Hz), 6.84 (d, 1H, J=15.6 Hz), 6.76 (t, 1H, J=7.6 Hz), 3.94 (m, 1H), 3.48-3.35 (m, 2H), 2.82-2.53 (broad m, 9H), 2.01-1.95 (m, 1H), 1.74-1.71 (m, 1H), 1.00 (q, 6H, J=7.0 Hz).

The compounds described in the following table 6 were prepared by methods analogous to the synthetic methods described in example 31 above, but using the appropriate starting materials.

TABLE 6

| Example # | Structure | MW | MS (MH+) calc'd | MS (MH+) exp |
|---|---|---|---|---|
| 31-2 | 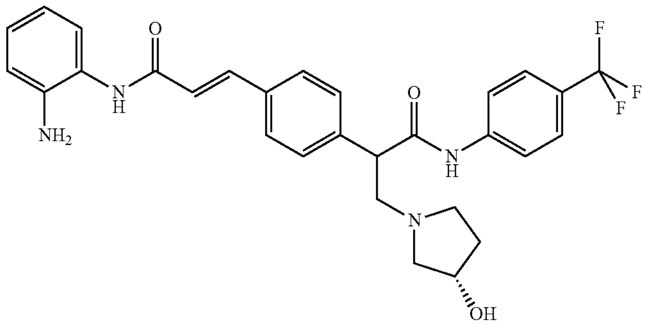 | 538.57 | 539 | 539 |
| 31-3 | 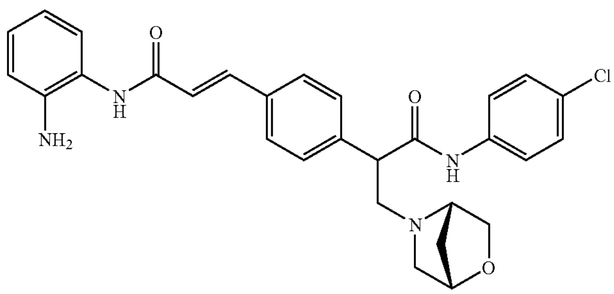 | 517.03 | 517 | 517 |
| 31-4 | 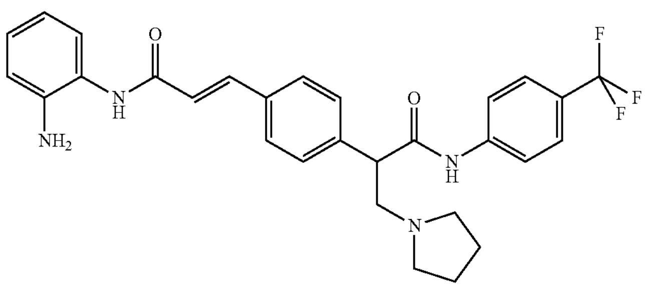 | 522.58 | 523 | 523 |
| 31-5 | 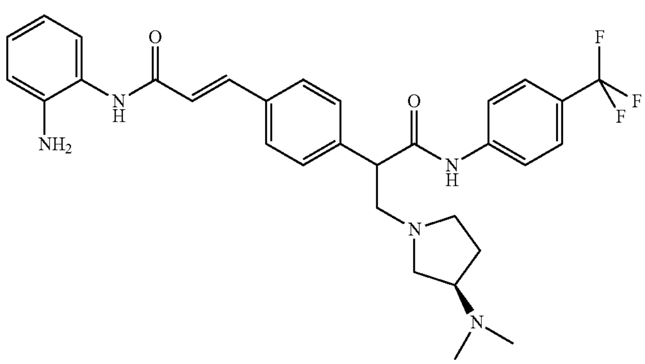 | 565.64 | 566 | 566 |
| 31-6 | 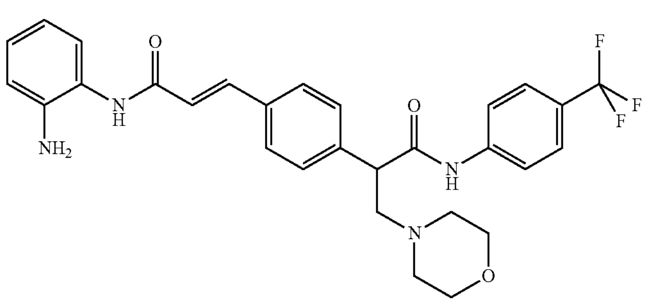 | 538.57 | 539 | 539 |

TABLE 6-continued

| Example # | Structure | MW | MS (MH+) calc'd | MS (MH+) exp |
|---|---|---|---|---|
| 31-7 | 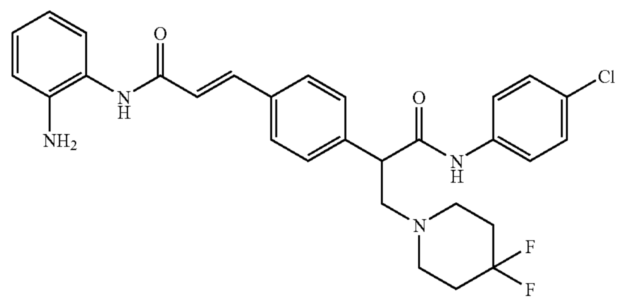 | 539.03 | 539 | 539 |
| 31-8 | 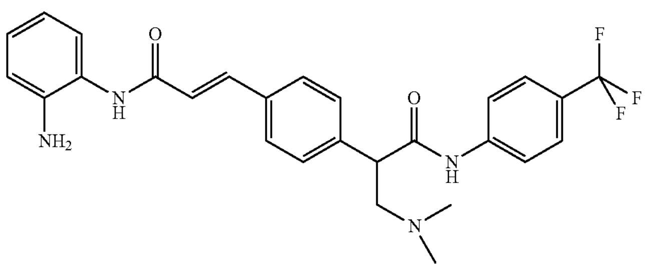 | 496.54 | 497 | 497 |
| 31-9 | 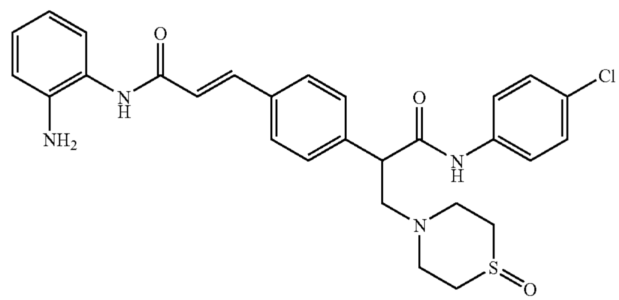 | 537.09 | 537 | 537 |

Example 32

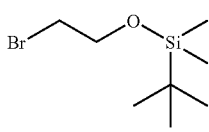

(2-Bromo-ethoxy)-tert-butyl-dimethyl-silane 2-bromoethanol (10.0 mL, 141 mmol) was added to a mixture of imidazole (12.5 g, 184 mmol) and tert-butyldimethylsilyl chloride (21.1 g, 140 mmol) in anhydrous DMF (25 mL). The reaction mixture was stirred at room temperature for 12 h, water and diethyl ether were added. The phases were separated. The aqueous phase was extracted with diethyl ether. The organic phase was washed with water and brine. The solution was dried with Na$_2$SO$_4$. Evaporation of the solvent yielded a colorless liquid. MS: calc'd 239 (MH+), exp 239 (MH+).

Example 33

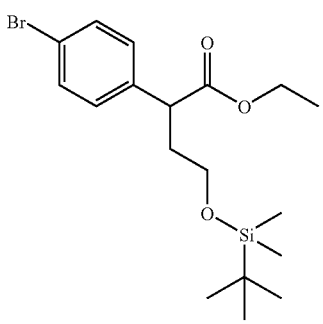

2-(4-Bromo-phenyl)-4-(tert-butyl-dimethyl-silanyloxy)-butyric acid ethyl ester A solution of (4-bromo-phenyl)-acetic acid ethyl (15 g, 61.7 mmol) and t-BuOK (10.3 g, 92.6 mmol) in DMF (50 mL) was stirred at room temperature for 1 h. Then (2-Bromo-ethoxy)-tert-butyl-dimethyl-silane (26.6 g, 111 mmol) was added slowly at 0 degrees Celsius to this solution. The mixture was stirred at room temperature overnight and poured into water (200 mL). The aqueous phase was extracted with EtOAc (200 mL×3), and the organic layer was washed with saturated NH$_4$Cl (200 mL), water (100 mL×3), brine (100 mL), dried with Na$_2$SO$_4$, and evaporated to get crude product. It was purified by flash chromatography (EtOAc/Hexane to CH$_2$Cl$_2$/MeOH) to obtain the desired product (12.1 g, 50%). MS: calc'd 401 (MH+), exp 401 (MH+).

Example 34

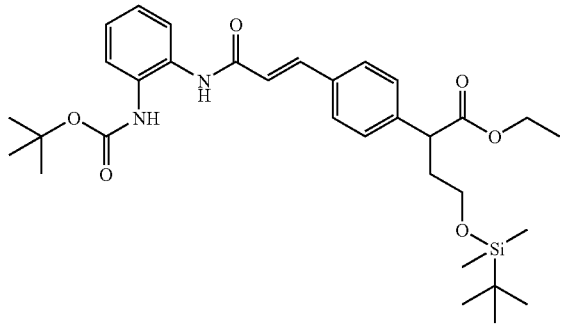

2-{4-[2-(2-tert-Butoxycarbonylamino-phenylcarbamoyl)-vinyl]-phenyl}-4-(tert-butyl-dimethyl-silanyloxy)-butyric acid ethyl ester A mixture of 2-(4-Bromo-phenyl)-4-(tert-butyl-dimethyl-silanyloxy)-butyric acid ethyl ester (4.5 g, 11.22 mmol), (2-acryloylamino-phenyl)-carbamic acid tert-butyl ester (3.1 g, 11.78 mmol), Pd$_2$(dba)$_3$ (839 mg, 0.92 mmol), tri-o-tolylphosphine (546 mg, 1.79 mmol) and triethylamine (4.53 g, 44.88 mmol) in DMF (50 mL) was stirred at 110 degrees Celsius under N2 for 4 hours. After cooling to room temperature, the mixture was poured into a saturated aqueous solution of NH$_4$Cl, and extracted with ethyl acetate (200 mL). The organic layer was washed with brine, dried over Na$_2$SO$_4$, filtered, concentrated in vacuo, and purified by flash column chromatography to obtain a pale yellow solid. (2.63 g, 42%). MS: calc'd 583 (MH+), exp 583 (MH+).

Example 35

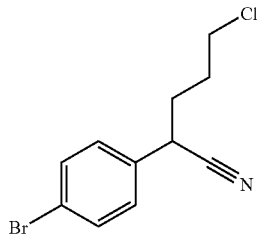

2-(4-Bromo-phenyl)-5-chloro-pentane nitrile

To a suspension of NaH (60%, 2.2 g, 55 mmol) dispersion in a mixture of DMF (30 mL)-Toluene (60 mL), 4-bromobenzeneacetonitirle (9.8 g, 50 mmol) was added under N2. After stirring and cooling on ice for 1 h, 3-Chloro-1-propyl bromide (7.87 g, 50 mmol) was added dropwise and stirring was continued for 30 min under 10 degrees Celsius, then water was added and the mixture and extracted with EtOAc. The organic layer was dried (MgSO$_4$) and evaporated in vacuo. The oily residue was distilled in vacuo giving an oil (5.4 g, 40%). by 155-160 degrees Celsius (7.5*10$^{-5}$ torr) MS: calc'd 271 (MH+), exp 271 (MH+). $^1$H NMR (400 MHz, CDCl$_3$), 7.54-7.56 (2H), 7.24-7.26 (2H), 3.84 (1H), 3.59 (2H), 1.92-2.12 (4H).

Example 36

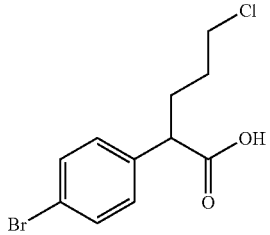

2-(4-bromophenyl)-5-chloro-pentanoic acid

The 2-(4-bromophenyl)-5-chloropentane nitrile (4 g, 14.7 mmol) was hydrolyzed by refluxing for 12 h with a 3:5:3 mixture of concentrated H$_2$SO$_4$, glacial acietic acid, and water (33 mL). The reaction mixture was cooled to room temperature, diluted with water, and extracted with CHCl$_3$. The organic layer was washed with brine (3 times), then dried with MgSO$_4$, the solution was evaporated to dryness under reduced pressure, giving an oil (3.8 g, 90%). MS: calc'd 290 (MH+), exp 290 (MH+). $^1$H NMR (400 MHz, CDCl$_3$), 7.46-7.56 (2H), 7.10-7.20 (2H), 3.84 (1H), 3.52 (3H), 1.60-2.20 (4H).

Example 37

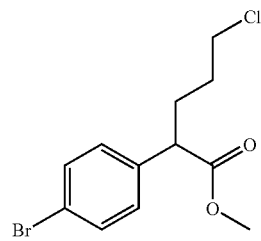

2-(4-Bromo-phenyl)-5-chloropentanoic acid methyl ester

To a solution of 2-(4-Bromo-phenyl)-5-chloropentanoic acid (3 g, 10.38 mmol) in MeOH (60 mL), SOCl$_2$ (2 mL) was added at 0 degrees Celsius, then the mixture refluxed for 5 h. After cooling, the solution was evaporated to dryness under reduced pressure, then EtOAc was added and the mixture was washed with aq. NaHCO$_3$, the organic layer was dried with MgSO₄, and evaporated to give the compound as an oil (2.85 g, 90%). MS: calc'd 304 (MH+), exp 304 (MH+).

Example 38

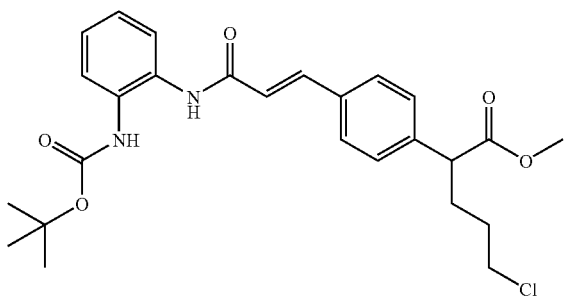

2-{4-[2-tert-Butoxycarbonylamino-phenylcarbamoyl)-vinyl]-phenyl}-5-chloro-pentanoic acid methyl ester A mixture of 2-(4-Bromo-phenyl)-5-chloropentanoic acid methyl ester (2 g, 6.67 mmol), (2-Acryloylamino-phenyl)-carbamic acid butyl ester (2 g, 7.2 mmol), Pd₂(dba)₃ (160 mg, 0.17 mmol), tri-o-tolylphosphine (160 mg, 0.53 mmol) and triethylamine (1.6 g, 15.8 mmol) in DMF (12 mL) was stirred at 100 degrees Celsius under N2 for 4 hours. The reaction mixture was diluted with EtOAc (80 mL), then washed with water (20 mL×2). The organic layer was dried by Na₂SO₄. The solution was evaporated. The residue product was finally purified by flash column chromatography to give the product (1.6 g, 50% yield). MS: calc'd 487 (MH+), exp 487 (MH+).

Example 39

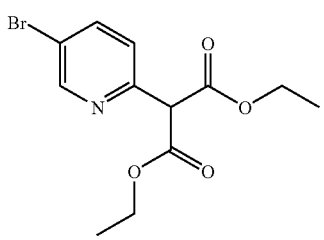

2-(5-Bromo-pyridin-2-yl)-malonic acid diethyl ester

A mixture of 5-bromo-2-iodo-pyridine (56.8 g, 0.2 mol), malonic acid diethyl ester (64 g, 0.4 mol), CuI (3.8 g, 0.02 mol), Cs₂CO₃ (195.5 g, 0.6 mol) and pyridine-2-carboxylic acid (2.46 g, 0.04 mol) in 1,4-dioxane (400 mL) was stirred at 70 degrees Celsius under N2 for 24 hours. After cooling to room temperature, the solid was filtered and the solvent was evaporated. The residue was dissolved in ethyl acetate (400 mL) and washed with water, brine, dried over Na₂SO₄, filtered, concentrated in vacuo, the crude product was purified by flash chromatography (Petroleum Ether:EtOAc=20:1) to obtain an oil (31.6 g, 50%). MS: calc'd 316 (MH+), exp 316 (MH+). ¹H NMR (d₆-DMSO, 400 MHz), 8.68 (d, 1H, J=2.4 Hz), 8.11 (dd, 1H, J=2.4, 8.4 Hz), 7.45 (d, 1H, J=8.4 Hz), 5.16 (s, 1H), 4.20-4.07 (m, 4H), 1.18 (t, J=8.4 Hz, 6H).

Example 40

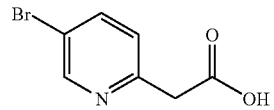

5-(Bromo-pyridin-2-yl)-acetic acid

To a solution of 2-(5-Bromo-pyridin-2-yl)-malonic acid diethyl ester (16.6 g, 52.5 mmol) in MeOH (200 mL) was added aq. NaOH (2N, 105 mL, 210 mmol). The solution was stirred at room temperature for 3 h, then concentrated in vacuo. The residue was dissolved in water and neutralized with 2N HCl to pH 3-4. Then the solid was filtered and washed with water, ether, dried to give a white solid product without further purification (9.0 g, 80%). MS: calc'd 215 (MH+), exp 215 (MH+).

Example 41

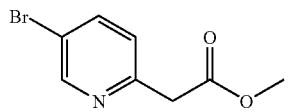

(5-Bromo-pyridin-2-yl)-acetic acid methyl ester

To a solution of 5-(Bromo-pyridin-2-yl)-acetic acid (9 g, 41.7 mmol) in MeOH (80 mL), SOCl₂ (10 g, 83.4 mmol) was added at 0 degrees Celsius, then the mixture stirred at room temperature for 3 h. After cooling, the solution was evaporated to dryness under reduced pressure, then EtOAc was added and the mixture was washed with aq. NaHCO₃, the organic layer was dried with MgSO₄, and evaporated to give the compound as an oil (8.6 g, 90%). MS: calc'd 229 (MH+), exp 229 (MH+).

Example 42

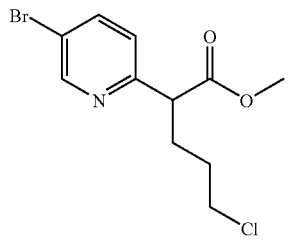

2-(5-Bromo-pyridin-2-yl)-5-chloro-pentanoic acid methyl ester

To a suspension of NaH (60%, 1.8 g, 44.9 mmol) dispersion in a mixture of DMF (60 mL), (5-Bromo-pyridin-2-yl)- acetic acid methyl ester (8.6 g, 37.4 mmol) was added under N2. After stirring and cooling on ice for 1 h, 3-chloro-1-propyl bromide (7.07 g, 44.9 mmol) was added dropwise and stirring was continued for 30 min under 10 degrees Celsius, then water was added and the mixture and extracted with EtOAc. The organic layer was dried (MgSO$_4$) and evaporated in vacuo. The oily residue was purified by chromatography (Petroleum ether:EtOAc=15:1) to give an oil (6.87 g, 60%). MS: calc'd 305 (MH+), exp 305 (MH+). $^1$H NMR (400 MHz, CDCl$_3$-d) 8.64 (d, 1H, J=2.4 Hz), 7.84 (dd, 1H, J=2.4, 8.4 Hz), 7.28 (s, 1H), 3.90-3.84 (m, 1H), 3.71 (s, 3H), 3.55 (t, 2H, J=6.4 Hz), 2.32-2.20 (m, 1H), 2.14-2.05 (m, 1H), 1.88-1.67 (m, 2H).

Example 43

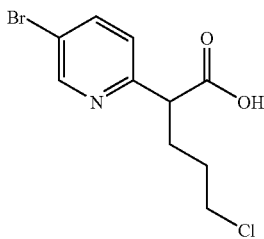

2-(5-Bromo-pyridin-2-yl)-5-chloro-pentanoic acid

To a solution of 2-(5-Bromo-pyridin-2-yl)-5-chloro-pentanoic acid methyl ester (2.0 g, 6.5 mmol) in THF/MeOH (5/1) 30 mL, LiOH.H$_2$O (1.092 g, 26 mmol.) was added. After the solution was stirred at room temperature for 16 h, the solution was neutralized with 2N HCl to pH 5-6. The mixture was evaporated to dryness under reduced pressure, then EtOAc (50 mL) was added. The organic layer was washed with brine, dried with Na$_2$SO$_4$, filtered, and evaporated to obtain of an oil product without further purification. MS: calc'd 291 (MH+), exp 291 (MH+).

Example 44

HDAC Inhibition by Novel Compounds: HeLa Extract HDAC Fluorometric Assay

Novel compounds were tested for their ability to inhibit histone deacetylase using an in vitro deacetylation assay. The enzyme source for this assay was HeLa nuclear extract. The substrate consisted of a commercial product containing an acetylated lysine side chain (both HeLa extract and substrate are available commercially from BIOMOL Research Laboratories, Inc., Plymouth Meeting, Pa.). After deacetylation of the substrate by incubation with HeLa nuclear extract, subsequent exposure to a developing reagent produces a fluorophore that is directly proportional to the level of deacetylation. Using the substrate concentration at the K$_m$ for the HeLa nuclear extract, the deacetylation assay was performed in the presence of novel compounds at 30 micromolar and the percent enzyme inhibition relative to a known reference HDAC inhibitor (SNDX-275) was determined. The compounds of the instant invention described in the Examples and Tables above exhibit histone deacetylase inhibitory activity in the range of about 75% to 190% relative to the known reference compound. Inhibitory activity for specific representative compounds can be found in Table 7.

Example 45 p21 Reporter Gene Induction by Novel Compounds

The novel compounds of the present invention were tested for their ability to induce p21 gene expression using a reporter gene assay involving HeLa cells transfected with a p21 promoter-luciferase construct. The p21 promoter contained the Sp1/Sp3 binding site for HDAC but not the upstream p53 binding site. Briefly, the day before transfection, HeLa cells were seeded at 11,000 cells/well in a 96-well culture plate and incubated at 37 degrees Celsius in 5% CO$_2$ overnight. For transfection, the medium was removed and replaced with 100 microliters/well transfection media previously prepared as follows: 5 microliters serum-free DMEM, 0.15 microliters Fugene 6 reagent, 40 ng p21-luc, 10 ng GFP were mixed gently and incubated at room temperature for 30 minutes; then 98 microliters DMEM (with 10% FBS, 1% penicillin and streptomycin) was added to the DNA:Fugene 6 reagent complex and mixed gently. After incubating the cells for 24 hours at 37 degrees Celsius in 5% CO$_2$, fresh media and test compounds were added to the wells and the cells further incubated for 15 hours at 37 degrees Celsius in 5% CO$_2$. Cells were lysed by adding 80 microliters/well of a cell culture lysis reagent (Promega). 50 microliters of each lysate was taken for GFP detection using an excitation wavelength of 486 nm and detection at 527 nm. 100 microliters Luciferase assay reagent (Promega) was then added to every 20 microliters cell lysate for luminometer detection. The compounds of the instant invention described in the Examples and Tables above exhibit p21 induction activity in the range of about 25% to 300% relative to the known HDAC inhibitor (SNDX-275) at a concentration of 3 micromolar. Induction activity for specific representative compounds can be found in Table 7.

Example 46

Antiproliferative Activity Against Cancer Cell Lines by Novel Compounds

The novel compounds of the present invention were tested for their ability to inhibit growth of various cancer cell lines using in vitro growth inhibition assays described below.
MTS Assay
Cells were seeded in 96-well culture plates (200 microliters/well at different seeding concentrations depending on cell type) and incubated overnight at 37 degrees Celsius in 5% CO$_2$. After adding compound dilutions to the cells (DMSO concentration kept below 0.5%), the cells were incubated at 37 degrees Celsius in 5% CO$_2$ for 72 hours. The effects on proliferation were determined by addition of MTS reagent (Promega) according to the manufacturer's instruction, followed by incubation for 2 hours at 37 degrees Celsius in 5% CO$_2$, and finally recording the absorbance at 490 nm using an ELISA plate reader.
WST Assay
Similar to MTS assay except that the developer is the CCK-8 reagent (Dojindo) and the plate reader is set to 450 nm absorbance.

The compounds of the instant invention described in the Examples and Tables above inhibited growth of cancer cell lines with 72 hour GI$_{50}$ values in the range of about 400 nanomolar to greater than 6 micromolar. GI$_{50}$ and GI$_{90}$ values against SMMC-7721 liver cancer cells for specific representative compounds can be found in Table 7.

TABLE 7

Table 7. Biological activity data for selected examples from the present invention. HDAC (RP30) is the relative inhibitory potency compared with SNDX-275 at 30 micromolar; p21 (RP3) is the relative induction potency compared with SNDX-275 at 3 micromolar.

| Example | HD (RP30) | p21 (RP3) | $GI_{50}$ (micromolar) SMMC-7721 | $GI_{90}$ (micromolar) SMMC-7721 |
|---|---|---|---|---|
| SNDX-275 | 100% | 100% | 3.5 | 10.5 |
| 6 | 151% | 212% | 0.8 | 2.7 |
| 25 | 170% | 199% | 0.8 | 2.5 |
| 6-2 | 134% | 233% | 1.0 | 3.1 |
| 9-2 | 173% | 74% | 0.7 | 1.5 |
| 9-3 | 139% | 305% | 0.8 | 2.1 |
| 31 | 184% | 243% | 0.9 | 3.3 |
| 9-4 | 163% | 155% | 1.4 | 4.9 |
| 9-5 | 179% | 127% | 1.1 | 3.2 |
| 9 | 187% | 253% | 1.3 | 2.9 |

The invention claimed is:

1. A compound of formula I,

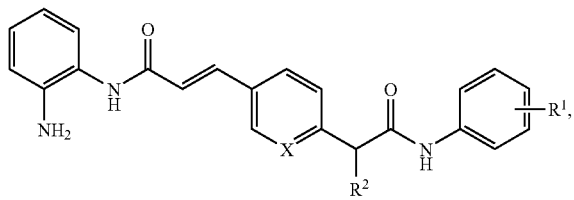

I wherein
$R^1$ is selected from the group consisting of:
hydrogen;
halogen;
lower alkyl, unsubstituted or once or several times substituted by halogen;
cycloalkyl;
cyano; and
lower alkoxy;
$R^2$ is —$(CH_2)_n$—$R^3$ or —$NR^4R^5$;
$R^3$ is a 3 to 10-membered heterocyclyl ring, unsubstituted or once or several times substituted by halogen, lower alkyl, hydroxy, —C(O)-lower alkoyl, =O, or $NR^4R^5$;
$R^4$ is hydrogen or lower alkyl;
$R^5$ is hydrogen or lower alkyl;
n is 0, 1, 2, or 3; and
X is C or N;
or a pharmaceutically active salt, racemic mixture, enantiomer, optical isomer or tautomeric form thereof.

2. A compound according to claim 1, wherein
$R^1$ is selected from the group consisting of:
halogen;
lower alkyl, unsubstituted or once or several times substituted by halogen; and
cycloalkyl.

3. A compound according to claim 1, wherein X is C.

4. A compound according to claim 1 wherein
$R^3$ is selected from the group consisting of: pyrrolidinyl, morpholinyl, piperidinyl, thiomorpholinyl, and 2-oxa-5-aza-bicyclo[2.2.1]heptanyl, wherein all the aforementioned rings may be unsubstituted or once or several times substituted by halogen, lower alkyl, hydroxy, —C(O)-lower alkyl, =O, or $NR^4R^5$; or $NR^4R^5$.

5. A compound according to claim 1, wherein said compound is selected from the group consisting of:
2-{4-[(E)-2-(2-Amino-phenylcarbamoyl)-vinyl]-phenyl}-5-morpholin-4-yl-pentanoic acid (4-bromo-phenyl)-amide;
2-{4-[(E)-2-(2-Amino-phenylcarbamoyl)-vinyl]-phenyl}-5-(1S,4S)-2-oxa-5-aza-bicyclo[2.2.1]hept-5-yl-pentanoic acid (4-trifluoromethyl-phenyl)-amide;
2-{4-[(E)-2-(2-Amino-phenylcarbamoyl)-vinyl]-phenyl}-5-(1S,4S)-2-oxa-5-aza-bicyclo[2.2.1]hept-5-yl-pentanoic acid (4-bromo-phenyl)-amide;
2-{4-[(E)-2-(2-Amino-phenylcarbamoyl)-vinyl]-phenyl}-5-morpholin-4-yl-pentanoic acid (4-isopropyl-phenyl)-amide;
2-{4-[(E)-2-(2-Amino-phenylcarbamoyl)-vinyl]-phenyl}-5-(1S,4S)-2-oxa-5-aza-bicyclo[2.2.1]hept-5-yl-pentanoic acid (4-isopropyl-phenyl)-amide;
2-{4-[(E)-2-(2-Amino-phenylcarbamoyl)-vinyl]-phenyl}-5-(3-hydroxy-piperidin-1-yl)-pentanoic acid (4-isopropyl-phenyl)-amide;
2-{4-[(E)-2-(2-Amino-phenylcarbamoyl)-vinyl]-phenyl}-5-(3-hydroxy-piperidin-1-yl)-pentanoic acid (4-bromo-phenyl)-amide;
2-{4-[(E)-2-(2-Amino-phenylcarbamoyl)-vinyl]-phenyl}-N-(4-bromo-phenyl)-4-morpholin-4-yl-butyramide;
2-{4-[(E)-2-(2-Amino-phenylcarbamoyl)-vinyl]-phenyl}-5-pyrrolidin-1-yl-pentanoic acid (4-trifluoromethyl-phenyl)-amide;
2-{4-[(E)-2-(2-Amino-phenylcarbamoyl)-vinyl]-phenyl}-5-piperidin-1-yl-pentanoic acid (4-bromo-phenyl)-amide;
2-{4-[(E)-2-(2-Amino-phenylcarbamoyl)-vinyl]-phenyl}-5-pyrrolidin-1-yl-pentanoic acid (4-bromo-phenyl)-amide;
2-{4-[(E)-2-(2-Amino-phenylcarbamoyl)-vinyl]-phenyl}-5-(2-oxa-5-aza-bicyclo[2.2.1]hept-5-yl)-pentanoic acid (4-chloro-phenyl)-amide;
(E)-N-(2-Amino-phenyl)-3-{4-[1-(4-chloro-phenylcarbamoyl)-2-(3-diethylamino-pyrrolidin-1-yl)-ethyl]-phenyl}-acrylamide;
2-{4-[(E)-2-(2-Amino-phenylcarbamoyl)-vinyl]-phenyl}-N-(4-bromo-phenyl)-4-(3-hydroxy-piperidin-1-yl)-butyramide;
2-{4-[(E)-2-(2-Amino-phenylcarbamoyl)-vinyl]-phenyl}-N-(4-bromo-phenyl)-4-(1S,4S)-2-oxa-5-aza-bicyclo[2.2.1]hept-5-yl-butyramide;
2-{4-[(E)-2-(2-Amino-phenylcarbamoyl)-vinyl]-phenyl}-N-(4-bromo-phenyl)-4-(1-methyl-pyrrolidin-2-yl)-butyramide; and
(E)-N-(2-Amino-phenyl)-3-{4-[1-(4-bromo-phenylcarbamoyl)-2-(1-methyl-piperidin-4-yl)-ethyl]-phenyl}-acrylamide.

6. A pharmaceutical composition comprising a compound according to claim 1 and a pharmaceutically acceptable adjuvant.

* * * * *